United States Patent
Halse et al.

(10) Patent No.: US 9,757,424 B2
(45) Date of Patent: Sep. 12, 2017

(54) COMPOSITIONS AND METHODS OF TREATING GLIOMAS

(71) Applicant: BioMed Valley Discoveries, Inc., Kansas City, MO (US)

(72) Inventors: Reza Halse, Kansas City, MO (US); Saurabh Saha, Leawood, KS (US); Jeffrey James Roix, Boston, MA (US)

(73) Assignee: Biomed Valley Discoveries, Inc., Kansas City, MO (US)

( * ) Notice: Subject to any disclaimer, the term of this patent is extended or adjusted under 35 U.S.C. 154(b) by 240 days.

(21) Appl. No.: 14/347,339

(22) PCT Filed: Sep. 25, 2012

(86) PCT No.: PCT/US2012/057085
§ 371 (c)(1),
(2) Date: Mar. 26, 2014

(87) PCT Pub. No.: WO2013/049045
PCT Pub. Date: Apr. 4, 2013

(65) Prior Publication Data
US 2014/0235556 A1    Aug. 21, 2014

Related U.S. Application Data

(60) Provisional application No. 61/539,779, filed on Sep. 27, 2011.

(51) Int. Cl.
| | |
|---|---|
| *A61K 31/4184* | (2006.01) |
| *A61K 38/08* | (2006.01) |
| *A61K 45/06* | (2006.01) |
| *A61K 31/41* | (2006.01) |
| *A61K 31/4188* | (2006.01) |
| *A61K 38/13* | (2006.01) |
| *A61K 31/137* | (2006.01) |
| *A61K 31/155* | (2006.01) |
| *A61K 31/165* | (2006.01) |
| *A61K 31/166* | (2006.01) |
| *A61K 31/167* | (2006.01) |
| *A61K 31/197* | (2006.01) |
| *A61K 31/235* | (2006.01) |
| *A61K 31/401* | (2006.01) |
| *A61K 31/403* | (2006.01) |
| *A61K 31/404* | (2006.01) |
| *A61K 31/4045* | (2006.01) |
| *A61K 31/4168* | (2006.01) |
| *A61K 31/4178* | (2006.01) |
| *A61K 31/42* | (2006.01) |
| *A61K 31/433* | (2006.01) |
| *A61K 31/4422* | (2006.01) |
| *A61K 31/472* | (2006.01) |

(Continued)

(52) U.S. Cl.
CPC ............ *A61K 38/08* (2013.01); *A61K 31/137* (2013.01); *A61K 31/155* (2013.01); *A61K 31/165* (2013.01); *A61K 31/166* (2013.01); *A61K 31/167* (2013.01); *A61K 31/197* (2013.01); *A61K 31/235* (2013.01); *A61K 31/401* (2013.01); *A61K 31/403* (2013.01); *A61K 31/404* (2013.01); *A61K 31/4045* (2013.01); *A61K 31/41* (2013.01); *A61K 31/4168* (2013.01); *A61K 31/4178* (2013.01); *A61K 31/4184* (2013.01); *A61K 31/4188* (2013.01); *A61K 31/42* (2013.01); *A61K 31/433* (2013.01); *A61K 31/4422* (2013.01); *A61K 31/472* (2013.01); *A61K 31/517* (2013.01); *A61K 31/5415* (2013.01); *A61K 31/55* (2013.01); *A61K 31/554* (2013.01); *A61K 31/675* (2013.01); *A61K 38/12* (2013.01); *A61K 38/13* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2006/0009506 A1 | 1/2006 | Westwick et al. | |
| 2006/0264384 A1* | 11/2006 | Johansen | A61K 31/366 514/27 |

(Continued)

FOREIGN PATENT DOCUMENTS

| | | |
|---|---|---|
| WO | 2006/122007 A1 | 11/2006 |
| WO | WO 2006122007 A1 * | 11/2006 |

OTHER PUBLICATIONS

Wilop et al. "Impact of angiotensin I converting enzyme inhibitors . . . ", 2009, J. Cancer Res. Clin. Oncol., vol. 135, pp. 1429-1435.*

(Continued)

*Primary Examiner* — Jeffrey S Lundgren
*Assistant Examiner* — Meghan Finn
(74) *Attorney, Agent, or Firm* — Bryan Cave LLP

(57) ABSTRACT

The present invention provides, inter alia, methods for treating or ameliorating the effects of a glioma. Methods of this invention include administering to a subject in need thereof an effective amount of a first active agent, such as e.g., an angiotensin receptor blocker, an antifungal agent, a bisphosphonate, an oxytocin inhibitor, an interleukin-1 (IL-1) inhibitor, a cyclooxygenase inhibitor, an α2δ voltage-dependent calcium channel (VDCC) inhibitor, a dihydroorotate dehydrogenase inhibitor, a calcium channel blocker, a renal sodium-chloride symporter inhibitor, an α2 adrenergic agonist, a phenothiazine antipsychotic, a calcineurin inhibitor, a 5-HT agonist, an angiotensin-converting enzyme (ACE) inhibitor, a direct rennin inhibitor, or combinations thereof, and a second active agent, which is a chemotherapeutic agent. Compositions for treating or ameliorating the effects of a glioma are also provided.

8 Claims, 19 Drawing Sheets

(51) Int. Cl.
*A61K 31/517* (2006.01)
*A61K 31/5415* (2006.01)
*A61K 31/55* (2006.01)
*A61K 31/554* (2006.01)
*A61K 31/675* (2006.01)
*A61K 38/12* (2006.01)

(56) References Cited

U.S. PATENT DOCUMENTS

| | | |
|---|---|---|
| 2007/0141066 A1 | 6/2007 | Phillips et al. |
| 2008/0076828 A1 | 3/2008 | Dalton et al. |
| 2009/0005321 A1 | 1/2009 | Zimmer et al. |
| 2009/0208583 A1* | 8/2009 | Rohrich ............... A61K 9/2077 424/495 |
| 2009/0220551 A1 | 9/2009 | Sampson et al. |
| 2010/0104651 A1 | 4/2010 | Gao et al. |
| 2010/0143485 A1 | 6/2010 | Hudnut et al. |
| 2010/0292335 A1 | 11/2010 | Campbell et al. |
| 2010/0298245 A1 | 11/2010 | Aydt et al. |

OTHER PUBLICATIONS

International Search Report, issued Jan. 25, 2013, for PCT/US2012/057085.
Stupp, R., et al. Radiotherapy plus concomitant and adjuvant temozolomide for glioblastoma. N Engl J Med. Mar. 10, 2005;352(10):987-96.
Written Opinion of the International Searching Authority, issued Jan. 25, 2013, for PCT/US2012/057085.

* cited by examiner

Figure 2
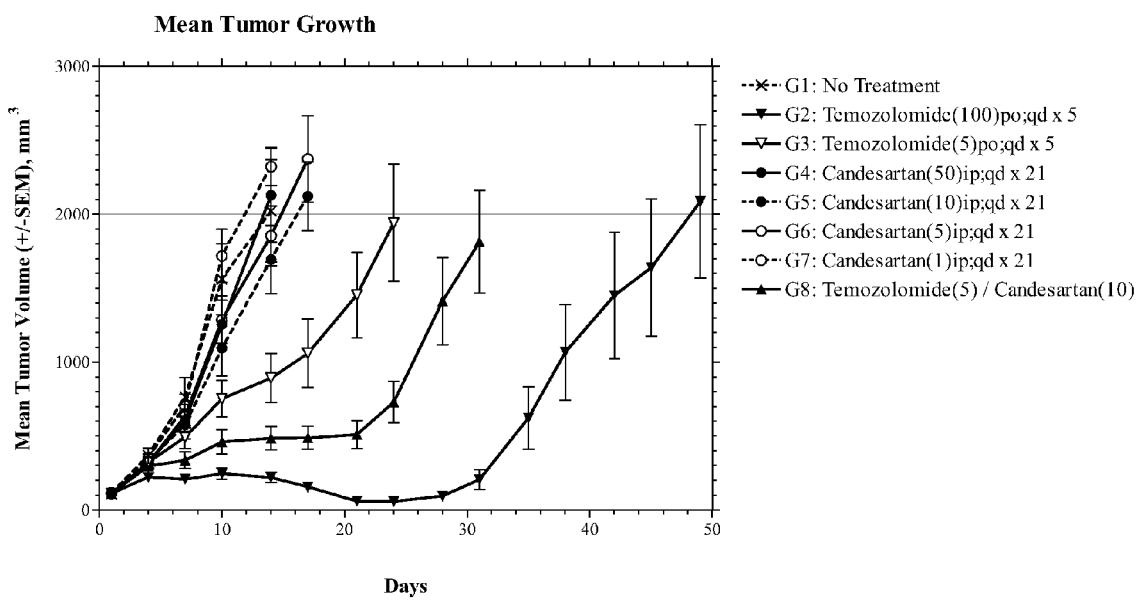
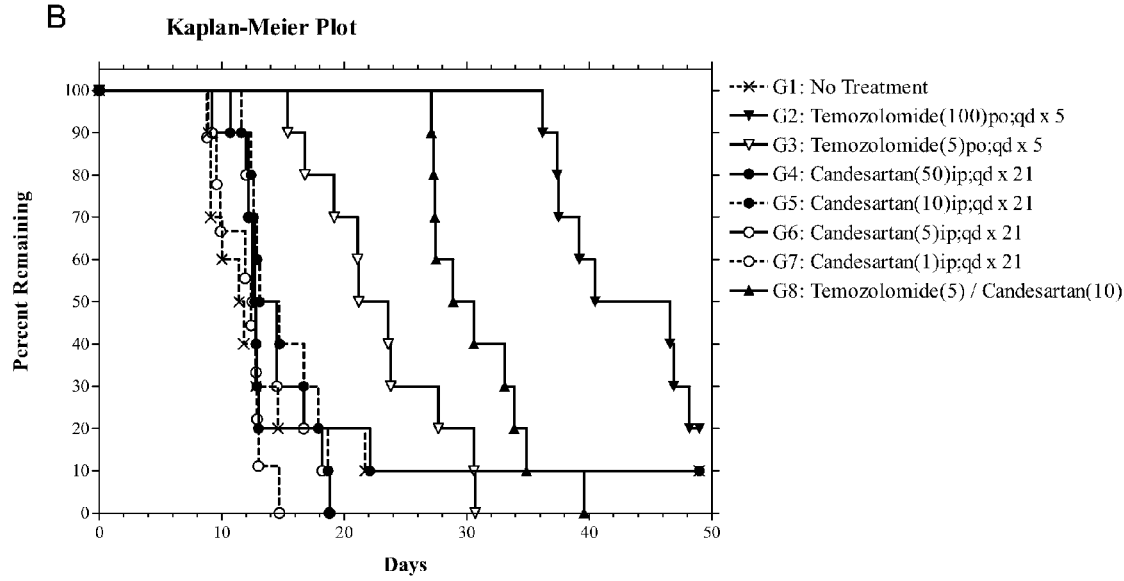

Figure 5
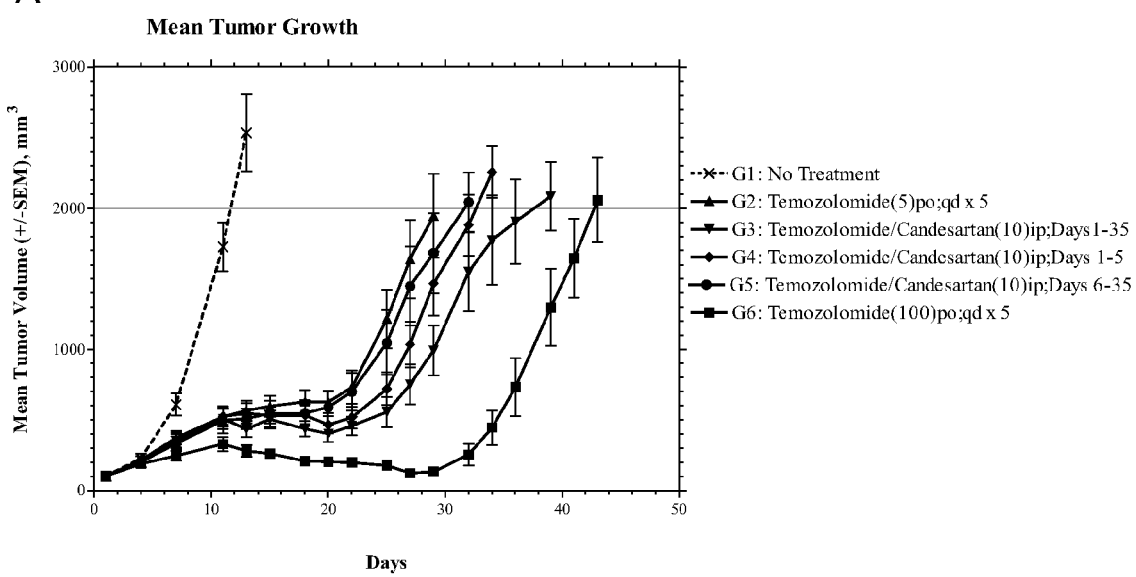
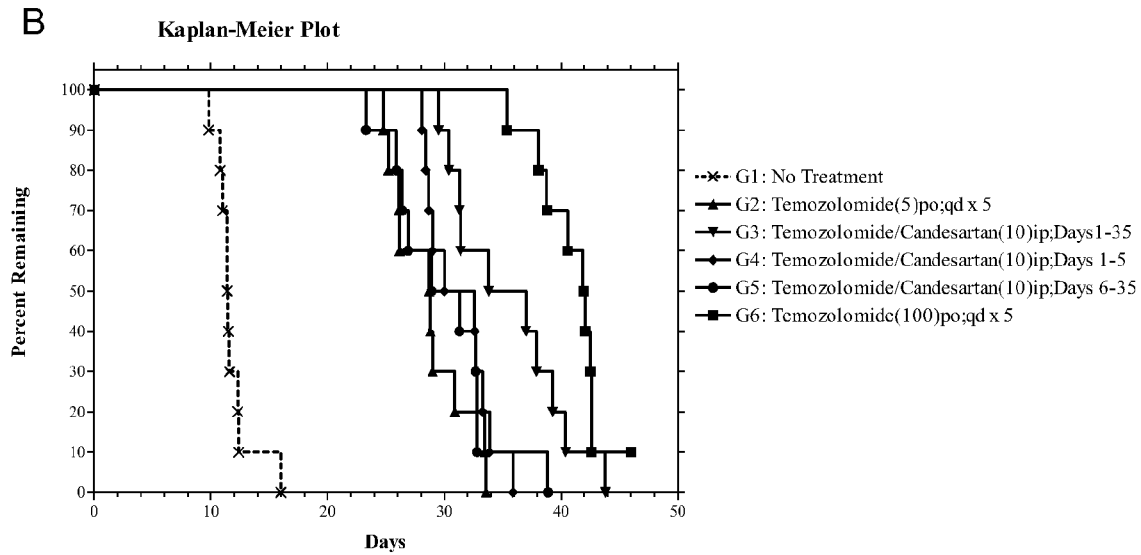

Figure 6
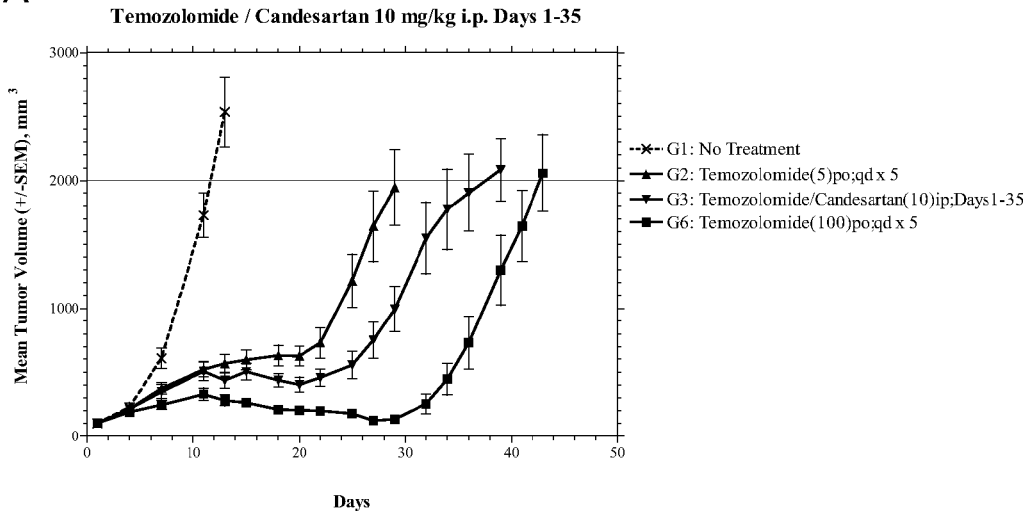
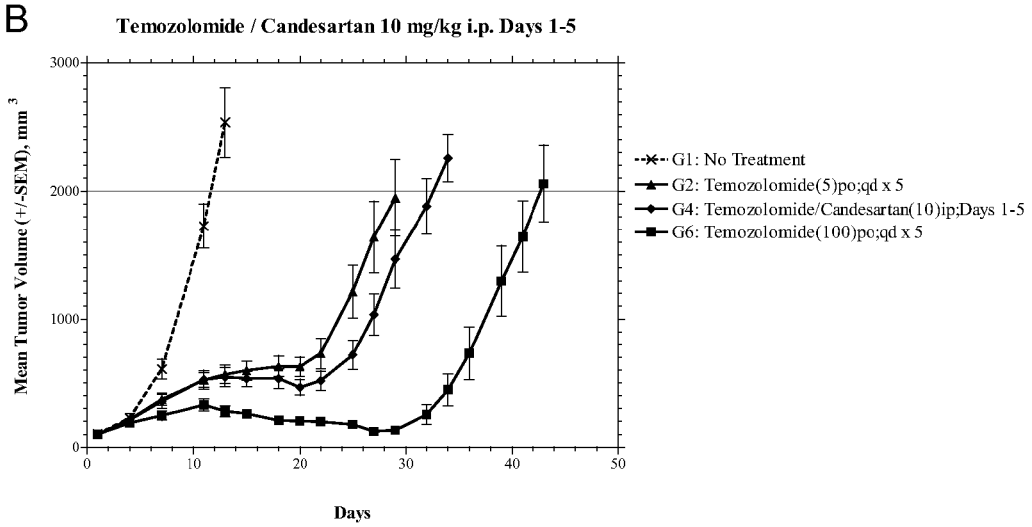
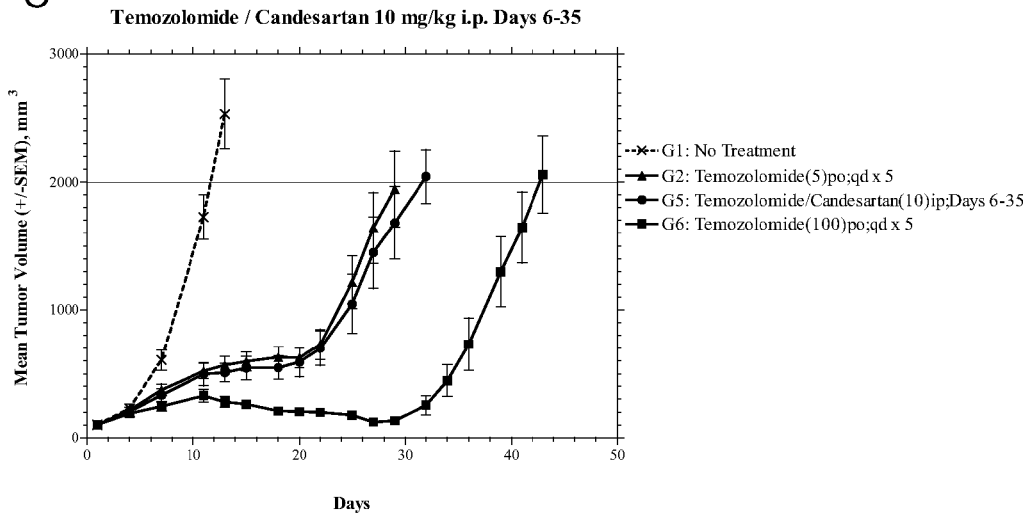

COMPOSITIONS AND METHODS OF TREATING GLIOMAS

CROSS-REFERENCE TO RELATED APPLICATIONS

The present invention is the National Stage of International Application No. PCT/US2012/057085 filed Sep. 25, 2012, which claims benefit to U.S. provisional application Ser. No. 61/539,779, filed Sep. 27, 2011. The entire contents of the above application are incorporated by reference as if recited in full herein.

FIELD OF THE INVENTION

This invention is directed to, inter alia, compositions and methods of treating gliomas.

BACKGROUND OF THE INVENTION

Gliomas are one of the most frequent types of nervous system tumors, making up 32% of the total diagnosed cases. Gliomas often carry a bleak prognosis and thus are among the most devastating diseases. Signs and symptoms depend on several factors (size, rate of growth, localization of the tumor) and are mainly represented by headaches, seizures, neurological deficits, and changes in mental status. The treatment for gliomas generally involves surgical removal, followed by a course of radiation and chemotherapy.

Glioblastoma, a malignant form of glioma, occurs more frequently than other types of primary central nervous system tumors. As for current therapy, temozolomide, an oral methylating chemotherapeutic agent, became the standard of care for newly diagnosed glioblastoma, when used concurrently with external beam radiation followed by adjuvant therapy. Even with the combination of radiotherapy plus temozolomide, median survival was 14.6 months at a median follow-up of 28 months (Stupp et al., New England J. Med., 352:987 (2005)). The two-year survival rate was 26.5 percent with radiotherapy plus temozolomide and 10.4 percent with radiotherapy alone (Id.).

Therefore, in spite of the introduction of temozolomide, further research for the development of new agents active against glioma is warranted. Indeed, there is still an unmet medical need for new potent agents for the treatment of gliomas. The present invention is directed to meeting this and other needs.

SUMMARY OF THE INVENTION

The present inventors have discovered that certain compounds disclosed herein, when used in combination with conventional chemotherapeutic agents, such as temozolomide, provide synergistic anti-tumor responses in a rodent model of glioma compared to conventional chemotherapeutic agents when used alone. These findings offer a new approach to the treatment of cancer, particularly unresectable and uncurable glioblastomas.

One embodiment of the present invention is a method for treating or ameliorating the effects of a glioma. This method comprises administering to a subject in need thereof an effective amount of a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an $\alpha 2\delta$ voltage-dependent calcium channel (VDCC) inhibitor, a dihydroorotate dehydrogenase inhibitor, a calcium channel blocker, a renal sodium-chloride symporter inhibitor, an $\alpha 2$ adrenergic agonist, a phenothiazine antipsychotic, a calcineurin inhibitor, a 5-hydroxytryptamine (5-HT) agonist, an angiotensin-converting enzyme (ACE) inhibitor, a direct rennin inhibitor, and combinations thereof, and a second active agent, which is a chemotherapeutic agent.

Another embodiment of the present invention is a composition for treating or ameliorating the effects of a glioma. This composition comprises a pharmaceutically acceptable carrier, a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an $\alpha 2\delta$ voltage-dependent calcium channel (VDCC) inhibitor, a dihydroorotate dehydrogenase inhibitor, a calcium channel blocker, a renal sodium-chloride symporter inhibitor, an $\alpha 2$ adrenergic agonist, a phenothiazine antipsychotic, a calcineurin inhibitor, a 5-HT agonist, an angiotensin-converting enzyme (ACE) inhibitor, a direct rennin inhibitor, and combinations thereof, and a second active agent, which is a chemotherapeutic agent.

Yet another embodiment of the present invention is a method for treating or ameliorating the effects of a glioblastoma. This method comprises co-administering to a subject in need thereof an effective amount of a first active agent selected from the group consisting of candesartan, terbinafine, risedronate, atosiban, diacerein, paracetamol, pregabalin, leflunomide, amlodipine, quinethazone, tizanidine, promazine, cyclosporin A, sumatriptan, a prodrug thereof, a pharmaceutically acceptable salt thereof, and combinations thereof, and a second active agent, which is temozolomide, a prodrug thereof, or a pharmaceutically acceptable salt thereof.

An additional embodiment of the present invention is a composition. This composition comprises a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an $\alpha 2\delta$ voltage-dependent calcium channel (VDCC) inhibitor, a dihydroorotate dehydrogenase inhibitor, a calcium channel blocker, a renal sodium-chloride symporter inhibitor, an $\alpha 2$ adrenergic agonist, a phenothiazine antipsychotic, a calcineurin inhibitor, a 5-HT agonist, an angiotensin-converting enzyme (ACE) inhibitor, a direct rennin inhibitor, and combinations thereof, and a second active agent, which is temozolomide, a prodrug thereof, or a pharmaceutically acceptable salt thereof; and a pharmaceutically acceptable carrier.

Yet another embodiment of the present invention is also a composition. This composition comprises a pharmaceutically acceptable carrier, a first active agent selected from the group consisting of candesartan, terbinafine, risedronate, atosiban, diacerein, paracetamol, pregabalin, leflunomide, amlodipine, quinethazone, tizanidine, promazine, cyclosporin A, sumatriptan, a prodrug thereof, a pharmaceutically acceptable salt thereof, and combinations thereof, and a second active agent, which is temozolomide, a prodrug thereof, or a pharmaceutically acceptable salt thereof.

BRIEF DESCRIPTION OF THE FIGURES

FIG. 2 shows a mean tumor growth plot (A) and a Kaplan-Meier plot (B) for groups treated with temozolomide and/or candesartan in comparison to no treatment control. The numbers in the parentheses in the legend on the right side of the graphs indicate the dose in mg/kg; ip indicates intraperitoneal administration; po indicates per os, or oral administration; qd×5 indicates once daily for five days (days 1-5); and qd×21 indicates once daily for 21 days. SEM: standard error of the mean.

FIG. 5 shows a mean tumor growth plot (A) and a Kaplan-Meier plot (B) for mice treated with different schedules of temozolomide and/or candesartan in comparison to no treatment control. The numbers in the parentheses of the legend to the right of the graphs indicate the dose in mg/kg. ip: intraperitoneal administration; po: oral administration; qd×5: once daily for five days (days 1-5); days 1-5: once daily from day 1 to day 5; days 1-35: once daily from day 1 to day 35; and days 6-35: once daily from day 6 to day 35. SEM: standard error of the mean.

FIGS. 6A-C show the mean tumor growth for groups treated with temozolomide and candesartan compared to temozolomide alone and a no treatment control for the number of days indicated. The numbers in the parentheses of the legend to the right of the graphs indicate the dose in mg/kg. ip: intraperitoneal administration; p.o.: oral administration; qd×5: once daily for five days (days 1-5); days 1-5: once daily from day 1 to day 5; days 1-35: once daily from day 1 to day 35; and days 6-35: once daily from day 6 to day 35. SEM: standard error of the mean.

DETAILED DESCRIPTION OF THE INVENTION

Figure 1:
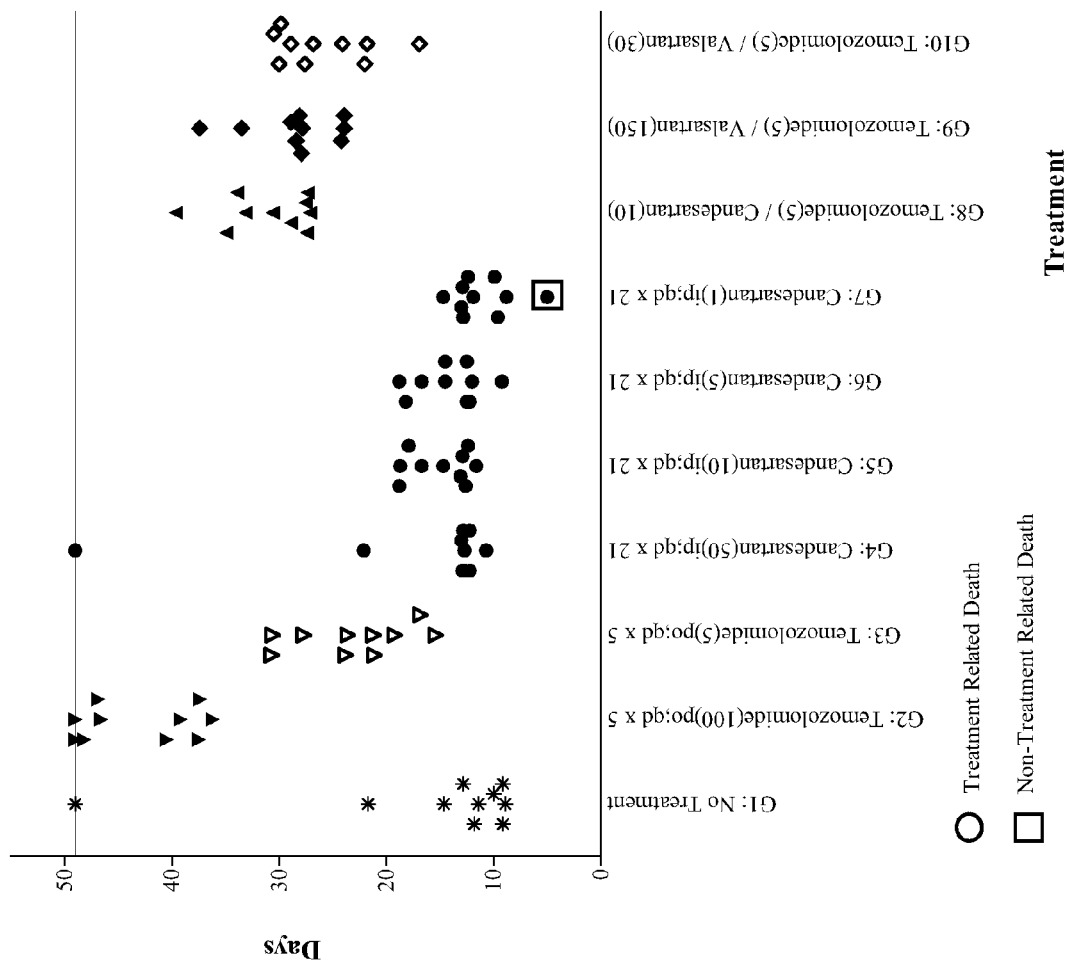
FIG. 1 shows the individual times to endpoint for mice treated with various doses of temozolomide, candesartan, or a combination of temozolomide and candesartan or temozolomide and valsartan in comparison to no treatment control. The numbers in the parentheses of the x-axis legend indicate the dose in mg/kg. ip: intraperitoneal administration; po: per os, or oral administration; qd×5: once daily for five days (days 1-5); and qd×21: once daily for 21 days.

One embodiment of the present invention is a method for treating or ameliorating the effects of a glioma. This method comprises administering to a subject in need thereof an effective amount of a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an α2δ voltage-dependent calcium channel (VDCC) inhibitor, a dihydroorotate dehydrogenase inhibitor, a calcium channel blocker, a renal sodium-chloride symporter inhibitor, an α2 adrenergic agonist, a phenothiazine antipsychotic, a calcineurin inhibitor, a 5-HT agonist, an angiotensin-converting enzyme (ACE) inhibitor, a direct rennin inhibitor, and combinations thereof, and a second active agent, which is a chemotherapeutic agent.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population.

Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, a "glioma" means a tumor or cancer of the glial cells of the nervous system. Gliomas generally start in the brain or the spine. There are three types of glial cells that can give rise to tumors or cancers. The glioma may be an astrocytoma, an oliogodendroglioma, an ependymoma, or a mixture thereof (also called mixed glioma). An astrocytoma is divided into four grades by the World Health Organization. Grade I, or a pilocytic astrocytoma, is characterized by slow growth, with relatively well-defined borders. In an embodiment of the invention, the glioma is an astrocytoma. Grade II, or low-grade astrocytoma, is characterized by slow growth, but with borders that are not well defined. Grade II gliomas rarely spread to other parts of the central nervous system. Grade III, or anaplastic astrocytoma, is characterized by relatively faster and more aggressive growth (in comparison to Grade II), with tumor cells non-uniform in appearance. Grade III gliomas invade neighboring tissues. Grade IV, or glioblastoma, is the most invasive type of glial tumors. Grade IV gliomas grow rapidly and commonly spread to nearby tissue. In an embodiment of the invention, the astrocytoma is a glioblastoma.

As used herein, a "subject" is a mammal, preferably, a human. In addition to humans, categories of mammals within the scope of the present invention include, for example, agricultural animals, domestic animals, laboratory animals, etc. Some examples of agricultural animals include cows, pigs, horses, goats, etc. Some examples of domestic animals include dogs, cats, etc. Some examples of laboratory animals include rats, mice, rabbits, guinea pigs, etc.

As used herein, a "chemotherapeutic agent" is a drug that may be used to treat cancer or tumor, such as, e.g., gliomas. Chemotherapeutic agents may be DNA damaging agents, antimetabolites, anti-microtubule agents, or antibiotic agents. DNA damaging agents include alkylating agents, intercalating agents, and enzyme inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, cisplatin, carboplatin, oxaliplatin, a pharmaceutically acceptable salt thereof, a prodrug thereof, and combinations thereof. Preferably, the DNA alkylating agent is temozolomide, a prodrug thereof, or a pharmaceutically acceptable salt thereof. Non-limiting examples of intercalating agents include doxorubicin, daunorubicin, idarubicin, and mitoxantrone. Non-limiting examples of enzyme inhibitors of DNA replication include irinotecan, topotecan, amsacrine, etoposide, etoposide phosphate, and teniposide. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, and decitabine. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicinepirubicin, bleomycin, plicamycin, and mitomycin.

As used herein, a "blocker" or "inhibitor" means a substance which can reduce the activity or the expression of the target protein. As used herein, an "agonist" means a substance which can activate a receptor, such as, e.g., the α2 adrenergic receptor or the 5-HT receptor.

In one aspect of this embodiment, the first active agent is an angiotensin receptor blocker. Angiotensin receptors are a class of G protein-coupled receptors with angiotensin II as their ligands. There are at least four subtypes of angiotensin receptors, type 1, type 2, type 3, and type 4. Preferably, the first active agent is a type 1 angiotensin receptor blocker. Type 1 angiotensin receptor blockers include, without limitation, candesartan, irbesartan, losartan, telmisartan, L158,809, saralasin, olmesartan, valsartan, a pharmaceutically acceptable salt thereof, a prodrug thereof, and combinations thereof. Preferably, the type 1 angiotensin receptor blocker is candesartan, valsartan, irbesartan, olmesartan, a pharmaceutically acceptable salt thereof, a prodrug thereof, or combinations thereof. More preferably, the type 1 angiotensin receptor blocker is candesartan, a prodrug thereof, or a pharmaceutically acceptable salt thereof. For example, the type 1 angiotensin receptor blocker may be candesartan cilexetil.

As used herein, a "prodrug" means a substance that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester to facilitate transmittal across a cell membrane, but which then is metabolically hydrolyzed to the active entity once inside the cell. Candesartan cilexetil is a non-limiting example of a prodrug (in this case, a prodrug of candesartan). Conventional procedures for the selection and preparation of suitable prodrug derivatives are described, for example, in Design of Prodrugs, (ed. H. Bundgaard, Elsevier, 1985), which is incorporated herein by reference for the purpose of describing procedures and preparation of suitable prodrug derivatives.

In another aspect of this embodiment, the first active agent is an antifungal agent. Non-limiting examples of antifungal agents include naftifine, butenafine, terbinafine, miconazole, ketoconazole, clotrimazole, econazole, omoconazole, bifonazole, butoconazole, fenticonazole, isoconazole, oxiconazole, sertaconazole, sulconazole, tioconazole, itraconazole, isavuconazole, ravuconazole, posaconazole, voriconazole, terconazole, albaconazole, abafungin, anidulafungin, caspofungin, micafungin, polygodia, tolnaftate, undecylenic acid, griseofulvin, haloprogin, a pharmaceutically acceptable salt thereof, a prodrug thereof, and combinations thereof. Preferably, the antifungal agent is terbinafine, a prodrug thereof, or a pharmaceutically acceptable salt thereof.

In yet another aspect of this embodiment, the first active agent is a bisphosphonate, which is a class of compounds that share a basic phosphate-carbon-phosphate core and bind strongly to calcium. Non-limiting examples of bisphosphonate include risedronate, alendronate, etidronate, clodronate, tiludronate, pamidronate, neridronate, olpadronate, ibandronate, zoledronate, a pharmaceutically acceptable salt thereof, a prodrug thereof, and combinations thereof. Preferably, the bisphosphonate is risedronate, a prodrug thereof, or a pharmaceutically acceptable salt thereof.

In an additional aspect of this embodiment, the first active agent is an oxytocin inhibitor. Non-limiting examples of oxytocin inhibitors include Barusiban (Fe200 440), GSK-221,149, L-368,899 (CAS #148927-60-0), L-371,257, L-372,662, SSR-126,768, WAY-162,720, atosiban, a pharmaceutically acceptable salt thereof, a prodrug thereof, and combinations thereof. Preferably, the oxytocin inhibitor is atosiban, a prodrug thereof, or a pharmaceutically acceptable salt thereof.

In another aspect of this embodiment, the first active agent is an IL-1 inhibitor. Non-limiting examples of IL-1 inhibitors include diacerein, interleukin-1 receptor antagonist (IL-1 RA), anakinra, rilonacept, a pharmaceutically acceptable salt thereof, a prodrug thereof, and combinations thereof. Preferably, the IL-1 inhibitor is diacerein, a prodrug thereof, or a pharmaceutically acceptable salt thereof.

In yet another aspect of this embodiment, the first active agent is a cyclooxygenase inhibitor. Non-limiting examples of cyclooxygenase inhibitors include paracetamol, aspirin (acetylsalicylic acid), diflunisal, salsalate, ibuprofen, naproxen, fenoprofen, ketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, licofelone, a pharmaceutically acceptable salt thereof, a prodrug thereof, and combinations thereof. Preferably, the cyclooxygenase inhibitor is paracetamol, a prodrug thereof, or a pharmaceutically acceptable salt thereof.

In an additional aspect of this embodiment, the first active agent is an α2δ VDCC inhibitor. Non-limiting examples of α2δ VDCC inhibitors include pregabalin, gabapentin, a pharmaceutically acceptable salt thereof, a prodrug thereof, and combinations thereof. Preferably, the α2δ VDCC inhibitor is pregabalin, a prodrug thereof, or a pharmaceutically acceptable salt thereof.

In another aspect of this embodiment, the first active agent is a dihydroorotate dehydrogenase inhibitor. Non-limiting examples of dihydroorotate dehydrogenase inhibitors include leflunomide, brequinar, 4SC-101 (2-(3-Fluoro-3'-methoxybiphenyl-4-carbamoyl)-cyclopent-1-enecarboxylic acid), a pharmaceutically acceptable salt thereof, a prodrug thereof, and combinations thereof. Preferably, the dihydroorotate dehydrogenase inhibitor is leflunomide, a prodrug thereof, or a pharmaceutically acceptable salt thereof.

In yet another aspect of this embodiment, the first active agent is a calcium channel blocker. Non-limiting examples of calcium channel blockers include amlodipine, verapamil, diltiazem, clevidipine, felodipine, isradipine, nifedipine, nicardipine, nimodipine, nisoldipine, aranidipine, azelnidipine, barnidipine, benidipine, cilnidipine, efonidipine, lacidipine, lercanidipine, manidipine, nilvadipine, nitrendipine, pranidipine, mibefradil, bepridil, fluspirilene, fendiline, a pharmaceutically acceptable salt thereof, a prodrug thereof, and combinations thereof. Preferably, the calcium channel blocker is amlodipine, diltiazem, lercanidipine, a prodrug thereof, a pharmaceutically acceptable salt thereof, or a combination thereof.

In an additional aspect of this embodiment, the first active agent is a renal sodium-chloride symporter inhibitor. Non-limiting examples of renal sodium-chloride symporter inhibitors include quinethazone, chlortalidone, hydrochlorothiazide, metolazone, bendroflumethiazide, naturetin, benzthiazide, chlorothalidone, chlorothiazide, hydroflumethiazide, indapamide, metolazone, methychothiazide, polythiazide, trichlormethiazide, a pharmaceutically acceptable salt thereof, a prodrug thereof, and combinations thereof. Preferably, the renal sodium-chloride symporter inhibitor is quinethazone, a prodrug thereof, or a pharmaceutically acceptable salt thereof.

In another aspect of this embodiment, the first active agent is an α2 adrenergic agonist. Non-limiting examples of α2 adrenergic agonists include tizanidine, dexmedetomidine, medetomidine, romifidine, clonidine, brimonidine, detomidine, lofexidine, xylazine, guanfacine, amitraz, a pharmaceutically acceptable salt thereof, a prodrug thereof, and combinations thereof. Preferably, the α2 adrenergic agonist is tizanidine, a prodrug thereof, or a pharmaceutically acceptable salt thereof.

In yet another aspect of this embodiment, the first active agent is a phenothiazine antipsychotic. Non-limiting examples of phenothiazine antipsychotics include promazine, chlorpromazine, triflupromazine, methotrimeprazine, mesoridazine, thioridazine, fluphenazine, perphenazine, prochlorperazine, trifluoperazine, a pharmaceutically acceptable salt thereof, a prodrug thereof, and combinations thereof. Preferably, the phenothiazine antipsychotic is promazine, a prodrug thereof, or a pharmaceutically acceptable salt thereof.

In an additional aspect of this embodiment, the first active agent is a calcineurin inhibitor. Non-limiting examples of calcineurin inhibitors include cyclosporin A, tacrolimus, pimecrolimus, ISA247 (Isotechnika), a pharmaceutically acceptable salt thereof, a prodrug thereof, and combinations thereof. Preferably, the calcineurin inhibitor is cyclosporin A, a prodrug thereof, or a pharmaceutically acceptable salt thereof.

In yet another aspect of this embodiment, the first active agent is a 5-HT agonist. Non-limiting examples of 5-HT agonists include sumatriptan, rizatriptan, naratriptan, buspirone, gepirone, tandospirone, lasmiditan, LY-334,370 (Eli Lilly), lorcaserin, cisapride, almotriptan, frovatriptan, eletriptan, zolmiatriptan, a pharmaceutically acceptable salt thereof, a prodrug thereof, and combinations thereof. Preferably, the 5-HT agonist is sumatriptan, a prodrug thereof, or a pharmaceutically acceptable salt thereof.

In a further aspect of this embodiment, the first active agent is an ACE inhibitor. Non-limiting examples of ACE inhibitors include captopril, zofenopril, enalapril, ramipril, quinapril, perindopril, lisinopril, benazepril, imidapril, fosinopril, trandolapril, casokinins, lactokinins, lactotripeptides (such as Val-Pro-Pro and Ile-Pro-Pro), a pharmaceutically acceptable salt thereof, a prodrug thereof, and combinations thereof. Preferably, the ACE inhibitor is ramipril, enalapril, benazepril, quinapril, a prodrug thereof, a pharmaceutically acceptable salt thereof, or combinations thereof.

In another aspect of this embodiment, the first active agent is a direct rennin inhibitor. Non-limiting examples of direct rennin inhibitors include CGP2928, aliskiren, a prodrug thereof, a pharmaceutically acceptable salt thereof, and combinations thereof. Preferably, the direct rennin inhibitor is aliskiren, a prodrug thereof, or a pharmaceutically acceptable salt thereof.

In an additional aspect of this embodiment, the first active agent and the second active agent are administered as part of a pharmaceutical composition.

Another embodiment of the present invention is a composition for treating or ameliorating the effects of a glioma. This composition comprises a pharmaceutically acceptable carrier, a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an α2δ voltage-dependent calcium channel (VDCC) inhibitor, a dihydroorotate dehydrogenase inhibitor, a calcium channel blocker, a renal sodium-chloride symporter inhibitor, an α2 adrenergic agonist, a phenothiazine antipsychotic, a calcineurin inhibitor, a 5-HT agonist, an ACE inhibitor, a direct rennin inhibitor, and combinations thereof, and a second active agent, which is a chemotherapeutic agent. The first and second active agents in this embodiment are as previously defined above.

In one aspect of this embodiment, the pharmaceutical composition is in a unit dosage form.

Yet another embodiment of the present invention is a method for treating or ameliorating the effects of a glioblastoma. This method comprises co-administering to a subject in need thereof an effective amount of a first active agent selected from the group consisting of candesartan, terbinafine, risedronate, atosiban, diacerein, paracetamol, pregabalin, leflunomide, amlodipine, quinethazone, tizanidine, promazine, cyclosporin A, sumatriptan, a prodrug thereof, a pharmaceutically acceptable salt thereof, and combinations thereof, and a second active agent, which is temozolomide, a prodrug thereof, or a pharmaceutically acceptable salt thereof. The first and second active agents in this embodiment are as previously defined above.

In the present invention, "co-administration" or "co-administering" means administration of two or more compounds together in the same composition, simultaneously in separate compositions, or as separate compositions administered at different times, as deemed most appropriate by a physician.

An additional embodiment of the present invention is a composition that comprises a first active agent selected from the group consisting of an angiotensin receptor blocker, an antifungal agent, a bisphosphonate, an oxytocin inhibitor, an interleukin-1 (IL-1) inhibitor, a cyclooxygenase inhibitor, an α2δ voltage-dependent calcium channel (VDCC) inhibitor, a dihydroorotate dehydrogenase inhibitor, a calcium channel blocker, a renal sodium-chloride symporter inhibitor, an α2 adrenergic agonist, a phenothiazine antipsychotic, a calcineurin inhibitor, a 5-HT agonist, an ACE inhibitor, a direct rennin inhibitor, and combinations thereof, and a second active agent, which is temozolomide, a prodrug thereof, or a pharmaceutically acceptable salt thereof; and a pharmaceutically acceptable carrier. The first and second active agents in this embodiment are as previously defined above.

Yet another embodiment of the present invention is a composition that comprises a pharmaceutically acceptable carrier, a first active agent selected from the group consisting of candesartan, terbinafine, risedronate, atosiban, diacerein, paracetamol, pregabalin, leflunomide, amlodipine, quinethazone, tizanidine, promazine, cyclosporin A, sumatriptan, a prodrug thereof, a pharmaceutically acceptable salt thereof, and combinations thereof, and a second active agent, which is temozolomide, a prodrug thereof, or a pharmaceutically acceptable salt thereof.

Another embodiment of the present invention is a method for treating a glioma. This method comprises administering to a subject in need thereof an effective amount of any composition disclosed herein.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a composition according to the invention will be that amount of the composition, which is the lowest dose effective to produce the desired effect. The effective dose of a compound or composition of the present invention may be administered as two, three, four, five, six or more sub-doses, administered separately at appropriate intervals throughout the day.

A suitable, non-limiting example of a dosage of a first active agent according to the present invention is from about 1 mg/kg to about 2400 mg/kg per day, such as from about 1 mg/kg to about 1200 mg/kg per day, including from about 50 mg/kg to about 1200 mg/kg per day. Other representative dosages of such agents include about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. For example, candesartan cilexetil may be administered at about 1-50 mg per day, preferably at about 2-32 mg per day. The effective dose of the first active agent in the compositions of the present invention may be administered as two, three, four, five, six or more sub-doses, administered separately at appropriate intervals throughout the day.

A suitable, non-limiting example of a dosage of a second active agent according to the present invention is from about 0.1 to 1000 $mg/m^2/day$, such as from about 0.5 mg/day to about 500 $mg/m^2/day$, including from about 50 $mg/m^2/day$ to about 200 $mg/m^2/day$. Other representative dosages of such an agent include about 0.2 $mg/m^2/day$, 0.5 $mg/m^2/day$, 0.7 $mg/m^2/day$, 1 $mg/m^2/day$, 1.2 $mg/m^2/day$, 1.5 $mg/m^2/day$, 2 $mg/m^2/day$, 3 $mg/m^2/day$, 4 $mg/m^2/day$, 5 $mg/m^2/day$, 6 mg/day, 7 $mg/m^2/day$, 8 $mg/m^2/day$, 9 $mg/m^2/day$, 10 $mg/m^2/day$, 15 $mg/m^2/day$, 20 $mg/m^2/day$, 25 $mg/m^2/day$, 30 $mg/m^2/day$, 35 $mg/m^2/day$, 40 $mg/m^2/day$, 45 $mg/m^2/day$, 50 $mg/m^2/day$, 55 $mg/m^2/day$, 60 $mg/m^2/day$, 65 $mg/m^2/day$, 70 $mg/m^2/day$, 75 $mg/m^2/day$, 80 $mg/m^2/day$, 85 $mg/m^2/day$, 90 $mg/m^2/day$, 95 $mg/m^2/day$, 100 $mg/m^2/day$, 110 $mg/m^2/day$, 120 $mg/m^2/day$, 130 $mg/m^2/day$, 140 $mg/m^2/day$, 150 $mg/m^2/day$, 160 $mg/m^2/day$, 170 $mg/m^2/day$, 180 $mg/m^2/day$, 190 $mg/m^2/day$, 200 $mg/m^2/day$, 210 $mg/m^2/day$, 220 $mg/m^2/day$, 230 $mg/m^2/day$, 240 $mg/m^2/day$, 250 $mg/m^2/day$, 260 $mg/m^2/day$, 270 $mg/m^2/day$, 280 $mg/m^2/day$, 290 $mg/m^2/day$, 300 $mg/m^2/day$, 350 $mg/m^2/day$, 400 $mg/m^2/day$, 450 $mg/m^2/day$, 500 $mg/m^2/day$, 600 $mg/m^2/day$, 700 $mg/m^2/day$, 800 $mg/m^2/day$, 900 $mg/m^2/day$, and 1000 $mg/m^2/day$. For example, temozolomide may be administered at about 2.5-200 $mg/m^2$ per day, preferably at about 50-200 $mg/m^2$ per day, for 5 days during each 28-day cycle. The effective dose of a second active agent according to the present invention may be administered as two, three, four, five, six or more sub-doses, administered separately at appropriate intervals throughout the day.

A composition and/or agent of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition and/or agent of the present invention may be administered in conjunction with other treatments. A composition and/or agent of the present invention may be encapsulated or otherwise protected against gastric or other secretions, if desired.

As set forth above, the compositions of the present invention comprise one or more active agents in admixture with one or more pharmaceutically-acceptable carriers and, optionally, one or more other compounds, drugs, ingredients and/or materials. Regardless of the route of administration selected, the active agent(s) of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.).

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22) solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s)/agent(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient(s)/agent(s) can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions of the present invention for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions of the present invention which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions of the present invention suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The following examples are provided to further illustrate the methods and compositions of the present invention. These examples are illustrative only and are not intended to limit the scope of the invention in any way.

EXAMPLES

Example 1

Female athymic nude mice (nu/nu, Harlan) were 8 to 12 weeks old. Xenografts were initiated with U87MG human glioblastomas (Piedmont Research Center, Morrisville, N.C.) by serial subcutaneous transplantation in these mice. Each test mouse received a U87MG tumor fragment of the size 1 mm$^3$. When the average size of the tumors approached the target range of 80 to 120 mm$^3$, treatment with temozolomide alone or a combination of temozolomide and candesartan cilexetil (abbreviated as candesartan in the Examples) were initiated. Body weight and tumor size were monitored.

Temozolomide was dissolved in deionized water. It was administered at either 5 mg/kg orally (p.o.) per day or 100 mg/kg (p.o.) per day, once daily from day 1 to day 5 of the treatment (qd×5). Candesartan in 0.5% carboxymethyl cellulose was dissolved in deionized water and administered intraperitoneally (i.p.) at the dose of 10 mg/kg once daily from day 1 to day 21 (qd×21).

The endpoint of the experiment is a mean tumor weight in Control Group of 2000 mm$^3$ or 22 days, whichever comes first. At the study endpoint, the results are as shown in Table 1 below.

TABLE 1

| treatment | n | MTV (n) Day 22 | % TGI | Statistical Significance | No. of PR | No. of CR | Mean BW Nadir | No. of TR | No. of NTR |
|---|---|---|---|---|---|---|---|---|---|
| Temozolomide (5 mg/kg, p.o., qd×5) | 10 | 825 (115) | — | — | 0 | 0 | — | 0 | 0 |
| Temozolomide (5 mg/kg, p.o. qd×5) and candesartan (10 mg/kg, i.p., qd×21) | 5 | 133 (5) | 84 | *** | 0 | 0 | −3.9% Day 5 | 0 | 0 |

TABLE 1-continued

| treatment | n | MTV (n) Day 22 | % TGI | Statistical Significance | No. of PR | No. of CR | Mean BW Nadir | No. of TR | No. of NTR |
|---|---|---|---|---|---|---|---|---|---|
| No treatment | 5 | — | — | — | 0 | 0 | — | 0 | 0 |
| Temozolomide (100 mg/kg, p.o., qdx5) | 5 | 101 (5) | 88 | *** | 1 | 0 | −4% Day 5 | 0 | 0 | n = number of animals in a group not dead from accidental or unknown causes, or euthanized for sampling
% TGI = [1 − (T/C)] × 100 = Percent tumor growth inhibition, compared to temozolomide at 5 mg/kg.
Statistical Significance = Unpaired t-test:
ne = not evaluable,
ns = not significant,
* = P < 0.05,
** = P < 0.01,
*** = P < 0.001, compared to temozolomide at 5 mg/kg.
MTV (n) = mean tumor volume (mm$^3$) for the number of animals on the day of TGI analysis (includes animals with tumor volume at endpoint)
PR = partial regression;
CR = complete regression
Mean BW Nadir = lowest group mean body weight, as % change from Day 1; — indicates no decrease in mean body weight was observed
TR = treatment-related death;
NTR = non-treatment-related death The following table summarizes the statistical tests performed to compare treatment with temozolomide alone (5 mg/kg, p.o., qdx5) and combination treatment with temozolomide (5 mg/kg, p.o., qdx5) and candesartan (10 mg/kg, i.p., qdx21).

TABLE 2

| Groups Compared | temozolomide;po;qd × 5 (5 mg/kg) vs. temozolomide;po;qd × 5 (5 mg/kg) & candesartan;ip;qd × 21 (10 mg/kg) |
|---|---|
| Unpaired t-test | Welch's Correction Applied |
| P value | P < 0.0001 |
| P value summary | *** (p ≤ 0.001) |
| Are means signif. different? (P < 0.05) | Yes |
| One- or two-tailed P value? | Two-tailed |
| t, df | t = 6.623 df = 74 |
| How big is the difference? | |
| Mean ± SEM of the first group | 825.1 ± 95.03 N = 115 |
| Mean ± SEM of the second group | 133.0 ± 43.45 N = 5 |
| Difference between means | 692.1 ± 104.5 |
| 95% confidence interval | −900.6 to −483.6 |
| R squared | 0.3721 |
| F test to compare variances | |
| F, DFn, Dfd | 110.0, 114, 4 |
| P value | 0.0002 |
| P value summary | *** (p ≤ 0.001) |
| Are variances significantly different? | Yes |

Example 2

The experiment consisted of groups (n=10) of female athymic nude mice bearing subcutaneous U87MG xenografts (75-144 mm$^3$) on Day 1. Candesartan was evaluated as monotherapies at dosages of 1, 5, 10 and 50 mg/kg administered intraperitoneally (i.p.) on a once daily for twenty-one days (qdx21) schedule. The combinations of temozolomide (5 mg/kg p.o. qdx5) with candesartan (10 mg/kg i.p. qdx21) or valsartan (150 or 30 mg/kg i.p. qdx21) were also evaluated in comparison to temozolomide alone (5 mg/kg p.o. qdx5). The study included an untreated tumor growth control group and a positive control group that received temozolomide at 100 mg/kg p.o. qdx5. Dosing was initiated on Day 1, and tumors were measured twice each week until the study was ended on Day 49. Animals were monitored individually and each mouse was euthanized for endpoint when its tumor attained a volume of 2000 mm$^3$ (about 2 grams) or on the final day (Day 49), whichever came first. Tumor samples were collected at endpoint, and histopathology analyses were performed.

The time to endpoint (TTE) was calculated for each mouse. Treatment outcome was determined from percent tumor growth delay (% TGD), defined as the percent increase in median TTE of treated versus control mice, with differences in the TTE values between groups deemed statistically significant at P 0.05 using logrank survival analysis. Animals were also monitored for partial regression (PR) and complete regression (CR) responses. Treatment tolerability was assessed by body weight measurements and frequent observation for signs of treatment-related (TR) toxicity.

The untreated control group had a median TTE of 11.6 days, establishing a maximum possible TGD of 37.4 days (322%) for this study. One 49-day survivor in this group reduced the power of the logrank test to detect significant differences between treated and control mice. The positive control for this model produced TGD of 32.0 days (276%), five regressions, and significant logrank survival (P=0.008), consistent with expected activity. All treatments were acceptably tolerated and could be evaluated for efficacy.

Treatment response was determined from an analysis of percent tumor growth delay (% TGD), defined as the percent increase in the median time to endpoint (TTE) in treated versus control mice; by logrank significance of differences in survival among treatment groups; and by regression responses. Plots of group mean tumor growth were also considered. Treatment tolerability was assessed by body weight measurements and frequent observation for clinical symptoms of treatment-related (TR) side effects.

Figure 3:
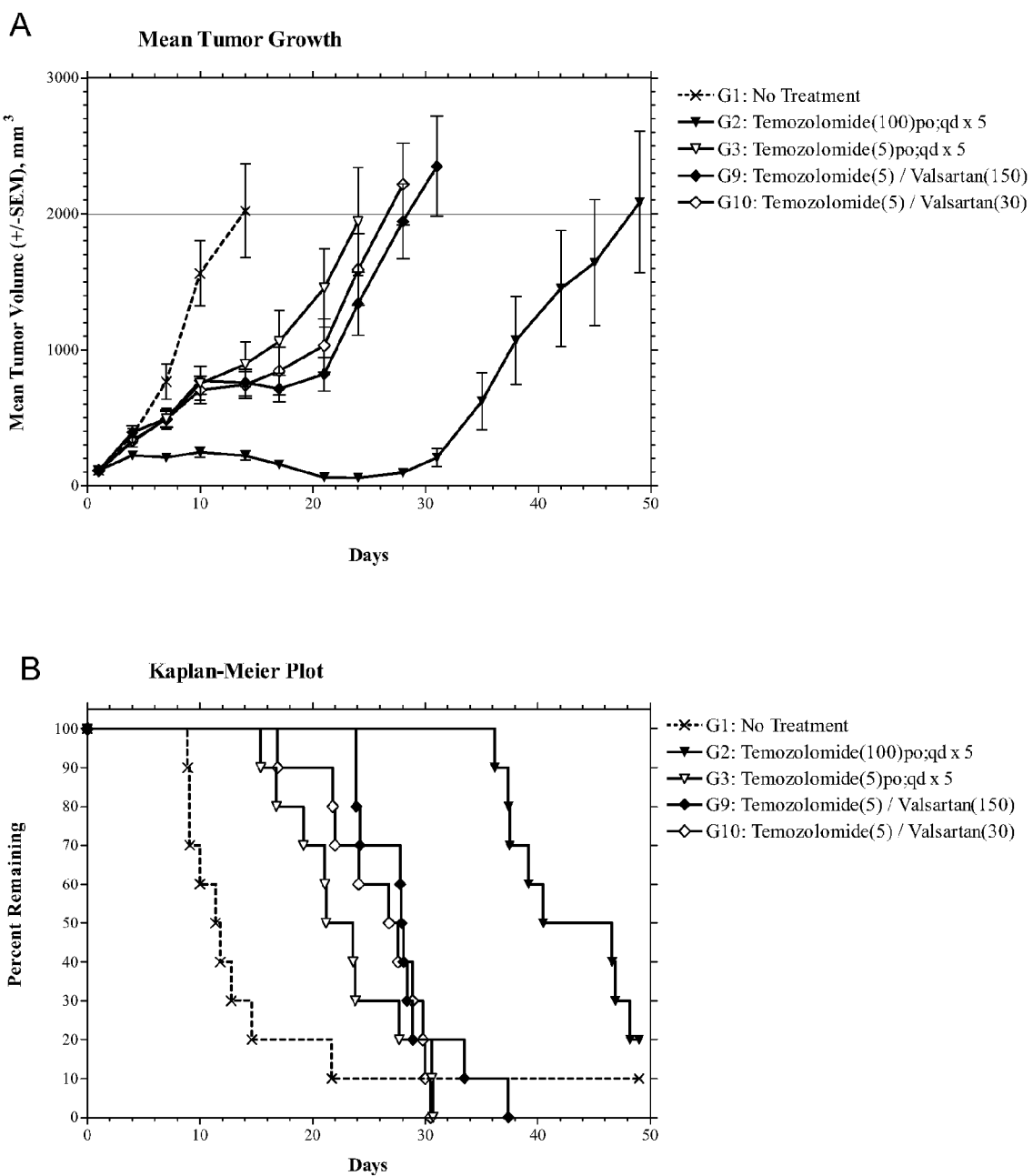
FIG. 3 shows a mean tumor growth plot (A) and a Kaplan-Meier plot (B) for groups treated with temozolomide and valsartan in comparison to no treatment control. The numbers in the parentheses in the legend on the right of the graphs indicate the dose in mg/kg; ip indicates intraperitoneal administration; po indicates oral administration; and qd×5 indicates once daily for five days (days 1-5). SEM: standard error of the mean.

Groups in this study were treated in accordance with the protocol summarized in Table 3, and the study was terminated on Day 49. Treatment responses are summarized in Table 4. FIG. 1 is a scatter plot showing the individual times to endpoint for each animal, by group. FIGS. 2-3 present plots of group mean tumor growth (upper panels) and Kaplan-Meier survival (lower panels) for the mono- and/or combination therapy groups treated with candesartan and valsartan, respectively.

TABLE 3

Protocol Design

| Group | n | Treatment Regimen 1 | | | | Treatment Regimen 2 | | | |
|---|---|---|---|---|---|---|---|---|---|
| | | Agent | Mg/kg | Route | Schedule | Agent | mg/kg | Route | Schedule |
| 1 | 10 | No Treatment | — | — | — | No Treatment | — | — | — |
| 2 | 10 | Temozolomide | 100 | po | qd x 5 | — | — | — | — |
| 3 | 10 | Temozolomide | 5 | po | qd x 5 | — | — | — | — |
| 4 | 10 | Candesartan | 50 | ip | qd x 21 | — | — | — | — |
| 5 | 10 | Candesartan | 10 | ip | qd x 21 | — | — | — | — |
| 6 | 10 | Candesartan | 5 | ip | qd x 21 | — | — | — | — |
| 7 | 10 | Candesartan | 1 | ip | qd x 21 | — | — | — | — |
| 8 | 10 | Temozolomide | 5 | po | qd x 5 | Candesartan | 10 | ip | qd x 21 |
| 9 | 10 | Temozolomide | 5 | po | qd x 5 | Valsartan | 150 | ip | qd x 21 |
| 10 | 10 | Temozolomide | 5 | po | qd x 5 | Valsartan | 30 | ip | qd x 21 |

TABLE 4

| Group | n | Treatment Regimen | | | | Median TTE | T−C | % TGD | Statistical Significance | | | MTV (n) Day 49 | Regressions | | | Mean BW Nadir | Deaths | |
|---|---|---|---|---|---|---|---|---|---|---|---|---|---|---|---|---|---|---|
| | | Agent | mg/kg | Route | Schedule | | | | vs G1 | vs G3 | vs G5 | | PR | CR | TFS | | TR | NTR |
| 1 | 10 | No Treatment | — | — | — | 11.6 | — | — | — | — | — | 14 (1) | 1 | 0 | 0 | — | 0 | 0 |
| 2 | 10 | Temozolomide | 100 | po | qd x 5 | 43.6 | 32.0 | 276 | ** | — | — | 0 (2) | 3 | 2 | 2 | — | 0 | 0 |
| 3 | 10 | Temozolomide | 5 | po | qd x 5 | 22.4 | 10.8 | 93 | ns | — | — | — | 0 | 0 | 0 | — | 0 | 0 |
| 4 | 10 | Candesartan | 50 | Ip | qd x 21 | 12.7 | 1.1 | 9 | ns | — | — | 1 (1) | 0 | 1 | 1 | — | 0 | 0 |
| 5 | 10 | Candesartan | 10 | Ip | qd x 21 | 13.9 | 2.3 | 20 | ns | — | — | — | 0 | 0 | 0 | — | 0 | 0 |
| 6 | 10 | Candesartan | 5 | Ip | qd x 21 | 13.5 | 1.9 | 16 | ns | — | — | — | 0 | 0 | 0 | — | 0 | 0 |
| 7 | 9 | Candesartan | 1 | ip | qd x 21 | 12.4 | 0.8 | 7 | ns | — | — | — | 0 | 0 | 0 | — | 0 | 1 |
| 8 | 10 | Temozolomide Candesartan | 5 10 | po ip | qd x 5 qd x 21 | 29.7 | 18.1 | 156 | * | ** | *** | — | 0 | 0 | 0 | — | 0 | 0 |
| 9 | 10 | Temozolomide Valsartan | 5 150 | po ip | qd x 5 qd x 21 | 28.0 | 16.4 | 141 | * | ns | — | — | 0 | 0 | 0 | — | 0 | 0 |
| 10 | 10 | Temozolomide Valsartan | 5 30 | po ip | qd x 5 qd x 21 | 27.2 | 15.6 | 134 | ns | ns | — | — | 0 | 0 | 0 | — | 0 | 0 |

The median TTE of Group 1 controls was 11.6 days, establishing a maximum possible TGD of 37.4 days (322%) for this 49-day study (Table 4). Nine control tumors progressed to the 2000 mm$^3$ endpoint, and the other tumor had a PR and remained in the study on Day 49 with a volume of 14 mm$^3$. This 49-day survivor reduced the power of the logrank test to detect statistically significant survival differences between treated and control groups. The scatter plot shows a relatively uniform distribution of calculated TTE values for nine controls, with one "outlier" TTE corresponding to the 49-day survivor (FIG. 1). The Group 1 mean tumor growth plot illustrates the rapid progression of control tumors (FIGS. 2-3, upper panels).

Group 2 received temozolomide administered at 100 mg/kg p.o. qd×5, and served as the positive control for the experiment. The median TTE of Group 2 was 43.6 days, corresponding to TGD of 32.0 days (276%), with three PRs and two CRs that remained to be tumor-free survivors (TFSs) at study end (Table 4). All Group 2 tumors attained the 2000 mm$^3$ endpoint volume, excluding the two TFSs (Table 4). Logrank analysis detected a statistically significant survival difference for the 100 mg/kg temozolomide group compared to control (Group 1 vs. 2, P=0.008). The Group 2 mean tumor growth plot indicated noteworthy activity, with a decrease in tumor burden from Days 14 to 24, followed by resumed tumor growth (FIGS. 2-3, upper panels).

Group 3 received 5 mg/kg temozolomide p.o. qd×5, and served as the temozolomide monotherapy control for the combinations administered in Groups 8, 9, and 10. The median TTE of Group 3 was 22.4 days, corresponding to TGD of 10.8 days (93%), with no regressions, and statistically non-significant logrank survival compared to control (Group 1 vs. 3, P>0.05). All Group 3 tumors progressed to the 2000 mm$^3$ endpoint volume (Table 4). The Group 3 mean tumor growth plot suggested marginal delay compared to control (FIGS. 2-3).

The 50, 10, 5 and 1 mg/kg candesartan monotherapies (i.p. qd×21) resulted in median TTEs of 12.7, 13.9, 13.5 and 12.4 days, respectively, corresponding to negligible TGDs ranging from 0.8 day (7%) to 2.3 days (20%), and statistically non-significant logrank survival compared to control (Group 1 vs. 4, 5, 6 or 7, P>0.05). The 50 mg/kg group (Group 4) had one CR that remained a TFS on Day 49 (Table 4), which may have been due to treatment or to poor engraftment. The 1 mg/kg group (Group 7) had one accidental death recorded on Day 5, and the data for this animal were excluded from TGD analysis. All other tumors in Groups 4-7 progressed to the 2000 mm$^3$ endpoint volume (Table 4). The mean tumor growth plots for these groups were comparable to that of control Group 1, with overlapping SEMs (FIG. 2, upper panel).

The combination of temozolomide (5 mg/kg p.o. qd×5) with candesartan (10 mg/kg i.p. qd×21) resulted in a median TTE of 29.7 days, corresponding to TGD of 18.1 days (156%), with statistically significant logrank survival compared to control (Group 1 vs. 8, P=0.043). The TGD for this combination group was 7.3 days longer than in Group 3 that received temozolomide alone (Table 4). All Group 8 tumors progressed to the 2000 mm³ endpoint volume, and no regression responses were recorded (Table 4). This combination treatment produced significantly longer overall survival compared to the corresponding temozolomide or candesartan monotherapies (Group 3 vs. 8, P=0.009, Group 5 vs. 8, P<0.001). Consistent with the TGD and logrank outcomes, the mean tumor growth plot indicated greater activity for the temozolomide/candesartan combination relative to either corresponding monotherapy (FIG. 2, upper panel).

The combination of temozolomide (5 mg/kg p.o. qd×5) with valsartan at 150 or 30 mg/kg (i.p. qd×21) resulted in median TTEs of 28.0 and 27.2 days, respectively, corresponding to TGD of 16.4 days (141%) for Group 9 and 15.6 days (134%) for Group 10 (Table 4). All tumors in these two groups progressed to the 2000 mm³ endpoint, and no regression responses were recorded (Table 4). The temozolomide/150 mg/kg valsartan combination resulted in significant logrank survival compared to control (Group 1 vs. 9, P=0.042), and borderline non-significant logrank survival compared to the temozolomide treatment (Group 3 vs. 9, P=0.053). The temozolomide/30 mg/kg valsartan combination resulted in a borderline nonsignificant logrank survival difference compared to control (Group 1 vs. 10, P=0.051), and no significant survival difference from temozolomide alone (Group 3 vs. 10, P>0.05). The Group 9 mean tumor growth plot suggested slightly greater activity compared to temozolomide alone (Group 3), whereas the Group 10 plot was comparable to that of Group 3, with overlapping SEMs (FIG. 3, upper panel).

Table 4 provides a summary of maximum mean BW losses, TR and NTR deaths. Clinical symptoms were recorded when observed.

This experiment evaluated candesartan as a monotherapy, as well as the combinations of temozolomide with candesartan or valsartan, for in vivo efficacy in the U87MG human glioblastoma xenograft model.

All test treatments were acceptably tolerated and could be evaluated for efficacy.

The 5 mg/kg temozolomide monotherapy resulted in TGD of 10.8 days (93%), with no regressions and non-significant logrank survival (P>0.05). However, the TGD recorded for this group exceeded the duration of treatment (5 days).

The four candesartan monotherapy treatments produced negligible TGDs, and non significant logrank survival compared to the untreated control group (P>0.05). One TFS in the 50 mg/kg candesartan group may have been due to treatment or to poor tumor engraftment. Notably, the combination of temozolomide (5 mg/kg p.o. qd×5) with candesartan (10 mg/kg i.p. qd×21) was superior to either regimen given alone based upon TGD, logrank survival and mean tumor growth. However, the 18.1-day TGD for the temozolomide/candesartan combination was shorter than the duration of candesartan treatment (21 days).

The higher dosage valsartan regimen (150 mg/kg i.p. qd×21) may have added slightly to temozolomide (5 mg/kg p.o. qd×5). The 16.4-day TGD for the temozolomide/150 mg/kg valsartan group was 5.6 days longer compared to that for temozolomide alone, and the overall survival difference between these two groups was borderline non-significant (P=0.053). Further, the mean tumor growth plots suggested slight delay for the combination compared to temozolomide alone (FIG. 3, upper panel). The temozolomide/30 mg/kg valsartan combination was not as measurably different from temozolomide alone.

In summary, candesartan was not efficacious as monotherapy. The combinations of temozolomide with 10 mg/kg candesartan was efficacious, and was superior to temozolomide alone. The combination of temozolomide with 150 mg/kg valsartan was efficacious and may have been better than temozolomide alone, but the difference was not statistically significant.

Methods and Materials

Mice

Female athymic nude mice (nu/nu, Harlan) were 8 to 9 weeks old and had a body weight range of 16.7 to 25.6 grams on Day 1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-O'Cobs™ Laboratory Animal Bedding in static microisolators on a 12 hour light cycle at 21-22° C. (70-72° F.) and 40-60% humidity. The recommendations of the Guide for Care and Use of Laboratory Animals with respect to restraint, husbandry, surgical procedures, feed and fluid regulation, and veterinary care were complied with.

Tumor Implantation

Xenografts were initiated with U87MG human glioblastomas (Piedmont Research Center, Morrisville, N.C.) by serial subcutaneous transplantation in athymic nude mice. Each test mouse received a U87MG tumor fragment (1 mm³) implanted subcutaneously in the right flank, and the growth of tumors was monitored as the average size approached the target range of 80 to 120 mm³. Nine days later, designated as Day 1 of the study, the animals were pair matched into fifteen groups each consisting of ten mice with individual tumor volumes ranging from 75 to 144 mm³ and group mean tumor volumes from 111 to 113 mm³. Tumor volume was calculated using the formula:

$$\text{Tumor Volume (mm}^3\text{)} = w^2 \times l/2$$

where w=width and l=length in mm of a U87MG tumor. Tumor weight may be estimated with the assumption that 1 mg is equivalent to 1 mm³ of tumor volume.

Therapeutic Agents

Valsartan and candesartan were supplied as a dry powder, which was stored at room temperature. The valsartan and candesartan dry powders and doses were also protected from light.

Doses of valsartan and candesartan were each formulated weekly, and were stored at 4° C. Valsartan dosing solutions were formulated at concentrations of 15 and 3 mg/mL to yield the desired 150 and 30 mg/kg dosages, respectively, in a dosing volume of 0.2 mL per 20 grams body weight (10 mL/kg). The required amount of valsartan powder for the 15 mg/mL solution was suspended in sterile saline, then dissolved with 0.1 N NaOH and pH adjusted to 7.4 with 0.1 N HCl. The 3 mg/mL valsartan dosing solution was prepared by diluting an aliquot of the 15 mg/mL valsartan solution with sterile saline. Candesartan doses were formulated in 0.5% carboxymethyl cellulose (CMC) in deionized water at concentrations of 5, 1, 0.5 and 0.1 mg/mL to yield the desired 50, 10, 5 and 1 mg/kg dosages, respectively, in a dosing volume of 10 mL/kg.

Temozolomide (Temodar®, Schering Corporation, Merck & Co. Inc., Whitehouse Station, N.J., Lot #8RSA025) was prepared by suspending the contents of two 100 mg Temodar® capsules in 20 mL deionized water. This 10 mg/mL stock was used to dose the 100 mg/kg temozolomide group, and was further diluted with deionized water to 0.5 mg/mL for dosing the 5 mg/kg group. The temozolomide dosing solutions were stored at 4° C. protected from light during the 5-day dosing period.

Treatment

On Day 1 of the study, mice were sorted in fifteen groups each consisting of ten mice, and dosing was initiated according to the treatment plan summarized in Table 3 below. Temozolomide doses were administered orally (p.o.) once daily for five days (qd×5). Each test agent was administered intraperitoneally (i.p.) once daily for twenty-one days (qd× 21), unless otherwise indicated.

Group 1 was not treated and served as the control group for calculation of % TGD. Group 2 received temozolomide administered at 100 mg/kg, and served as the positive control for the model. Group 3 received temozolomide administered at 5 mg/kg, and served as the monotherapy control for the combination treatments. Groups 4-7 received candesartan at 50, 10, 5 or 1 mg/kg, respectively. Group 8 received the combination of 5 mg/kg temozolomide with 10 mg/kg candesartan. Groups 9 and 10 received the combinations of 5 mg/kg temozolomide with valsartan administered at 150 or 30 mg/kg, respectively. All doses were scaled to the body weights of the individual animals.

Endpoint

Tumors were measured twice each week using calipers. Animals were monitored individually, and each mouse was euthanized when its tumor reached the endpoint size of 2000 mm$^3$ or at the conclusion of the study (Day 49), whichever came first. The time to endpoint (TTE) for each mouse was calculated from the following equation:

$$\text{TTE (days)} = [\log_{10}(\text{endpoint volume, mm}^3) - b]/m$$

where b is the intercept and m is the slope of the line obtained by linear regression of a log-transformed tumor growth data set. The data set was comprised of the first observation that exceeded the study endpoint volume and the three consecutive observations that immediately preceded the attainment of the endpoint volume. Animals that do not reach the endpoint are assigned a TTE value equal to the last day of the study. Animals classified as NTR (non-treatment-related) deaths due to accident (NTRa) or due to unknown causes (NTRu) are excluded from TTE calculations (and all further analyses). Animals classified as TR (treatment-related) deaths or NTRm (non-treatment related death due to metastasis) are assigned a TTE value equal to the day of death.

Treatment outcome was evaluated by tumor growth delay (TGD), which is defined as the increase in the median time to endpoint (TTE) in a treatment group compared to the control group:

Treatment outcome was evaluated by tumor growth delay (TGD), which is defined as the increase in the median time to endpoint (TTE) in a treatment group compared to the control group:

$$TGD = T - C,$$

expressed in days, or as a percentage of the median TTE of the control group:

$$\% TGD = 100 \times (T-C)/C$$

Where:
T=median TTE for a treatment group,
C=median TTE for the control group (Group 1).

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. An animal with a CR response at the termination of a study is additionally classified as a tumor-free survivor (TFS). Animals were monitored for regression responses.

Sampling

At endpoint, tumor samples were collected from two animals in the control group (Group 1), and from three animals per group in Group 3 (5 mg/kg temozolomide), Group 8 (5 mg/kg temozolomide/10 mg/kg candesartan), and Group 9 (5 mg/kg temozolomide/150 mg/kg valsartan). Each tumor sample was preserved in 10% neutral buffered formalin for 16-24 hours then transferred to 70% ethanol. The preserved tumor samples were shipped to Biotechnics, Inc. (Hillsborough, N.C.) for hematoxylin and eosin (H&E) staining, as well as for KDR, CD-31, Ki-67 and cleaved caspase-3 analyses.

Toxicity

Animals were weighed daily on Days 1-5, and then twice weekly until the study was completed. The mice were observed frequently for overt signs of any adverse, treatment-related side effects, and clinical signs of toxicity were recorded when observed. Acceptable toxicity was defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 14 days of the last dose. A death is classified as NTR if there is no evidence that death was related to treatment side effects.

Statistical and Graphical Analyses

The logrank test, which evaluates overall survival experience, was used to analyze the significance of the differences between the TTE values of selected groups. The logrank test analyzes the individual TTEs for all animals in a group, except those lost to the study due to NTR death. Two-tailed statistical analyses were conducted at significance level P=0.05. Statistical analyses are not conducted for any group whose treatment is deemed above the MTD. Kaplan-Meier plots were constructed to show the percentage of animals remaining in the study as a function of time. These plots used the same data set as the logrank test.

Mean tumor growth curves show group mean tumor volumes as a function of time, with error bars indicating one standard error of the mean (SEM). When an animal exited the study due to tumor size, the final tumor volume recorded for the animal was included with the data used to calculate the group mean tumor volume at subsequent time points. Mean tumor growth plots were truncated after 50% of the animals in a group had exited the study for tumor volume endpoint or after the second TR death in a group, whichever came first.

Prism (GraphPad) for Windows 3.03 was used for all graphic presentations and statistical analyses.

Example 3

In this Example, candesartan administered on different schedules in combination with temozolomide were evaluated for efficacy in nu/nu mice bearing subcutaneous U87MG human glioblastoma xenografts.

Temozolomide (5 mg/kg p.o. qd×5) in combination with candesartan administered at 10 mg/kg i.p. were administered on three different schedules: once daily for thirty-five days (qd×35), once daily for five days (qd×5), and once daily for thirty days beginning on Day 6 (qd×30 start Day 6). The experiment included temozolomide monotherapy (5 mg/kg p.o. qd×5) and positive control (100 mg/kg p.o. qd×5) groups. An untreated group served as the control group for efficacy analysis. Dosing was initiated on Day 1, except where indicated otherwise, and tumors were measured twice each week until the study was ended on Day 46. Animals were monitored individually and each mouse was euthanized for endpoint when its tumor attained a volume of 2000 mm$^3$ (about 2 grams) or on the final day (Day 46), whichever came first. These treatment schedules are summarized in Table 5.

Treatment response was determined from an analysis of percent tumor growth delay (% TGD), defined as the percent increase in the median time to endpoint (TTE) in treated versus control mice; by logrank significance of differences in survival among treatment groups; and by regression responses. Plots of group mean tumor growth were also considered. Treatment tolerability was assessed by body weight measurements and frequent observation for clinical symptoms of treatment-related side effects. Treatment responses are summarized in Table 6.

TABLE 5

| | | Treatment Regimen 1 | | | | Treatment Regimen 2 | | | |
|---|---|---|---|---|---|---|---|---|---|
| Group | n | Agent | mg/kg | Route | Schedule | Agent | mg/kg | Route | Schedule |
| 1 | 10 | No Treatment | — | — | — | No Treatment | — | — | — |
| 2 | 10 | Temozolomide | 5 | po | qd x 5 | — | — | — | — |
| 3 | 10 | Temozolomide | 5 | po | qd x 5 | Candesartan | 10 | ip | qd x 35 |
| 4 | 10 | Temozolomide | 5 | po | qd x 5 | Candesartan | 10 | ip | qd x 5 |
| 5 | 10 | Temozolomide | 5 | po | qd x 5 | Candesartan | 10 | ip | qd x 30 (start Day 6) |
| 6 | 10 | Temozolomide | 100 | po | qd x 5 | — | — | — | — |

TABLE 6

| | | Treatment Regimen | | | | Median TTE | T − C | % TGD | Statistical Significance | | MTV (n) Day 46 | Regressions | | | Mean BW Nadir | Deaths | |
|---|---|---|---|---|---|---|---|---|---|---|---|---|---|---|---|---|---|
| Group | n | Agent | mg/kg | Route | Schedule | | | | vs G1 | vs G2 | | PR | CR | TFS | | TR | NTR |
| 1 | 10 | No Treatment | — | — | — | 11.4 | — | — | — | — | — | 0 | 0 | 0 | — | 0 | 0 |
| 2 | 10 | Temozolomide | 5 | po | qd x 5 | 28.7 | 17.3 | 152 | *** | — | — | 0 | 0 | 0 | — | 0 | 0 |
| 3 | 10 | Temozolomide Candesartan | 5 10 | po ip | qd x 5 qd x 35 | 35.4 | 24.0 | 211 | *** | *** | — | 0 | 0 | 0 | −1.1% Day 7 | 0 | 0 |
| 4 | 10 | Temozolomide Candesartan | 5 10 | po ip | qd x 5 qd x 5 | 31.3 | 19.9 | 175 | *** | ns | — | 0 | 0 | 0 | −0.3% Day 7 | 0 | 0 |
| 5 | 10 | Temozolomide Candesartan | 5 10 | po ip | qd x 5 qd x 30 (start Day 6) | 30.1 | 18.7 | 164 | *** | ns | — | 0 | 0 | 0 | — | 0 | 0 |
| 6 | 10 | Temozolomide | 100 | po | qd x 5 | 42 | 30.6 | 268 | *** | — | 0 (1) | 0 | 1 | 1 | −6.2% Day 7 | 0 | 0 |

Figure 4:
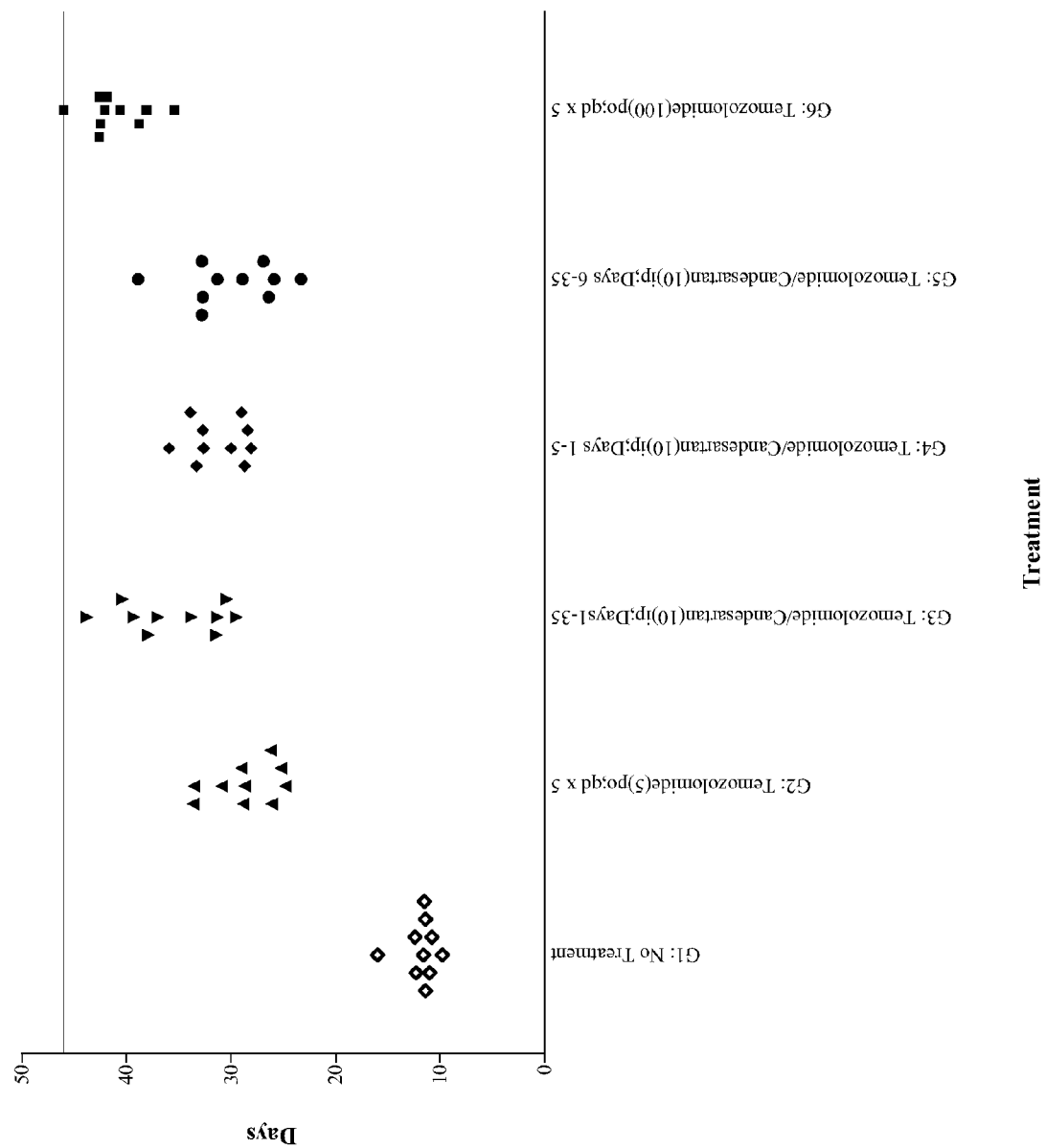
FIG. 4 shows the individual times to endpoint for mice treated with different schedules of temozolomide and/or candesartan in comparison to a no treatment control. The numbers in the parentheses of the x-axis legend indicate the dose in mg/kg. ip: intraperitoneal administration; po: oral administration; qd×5: once daily for five days (days 1-5); days 1-5: once daily from day 1 to day 5; days 1-35: once daily from day 1 to day 35; and days 6-35: once daily from day 6 to day 35.
Figure 7:
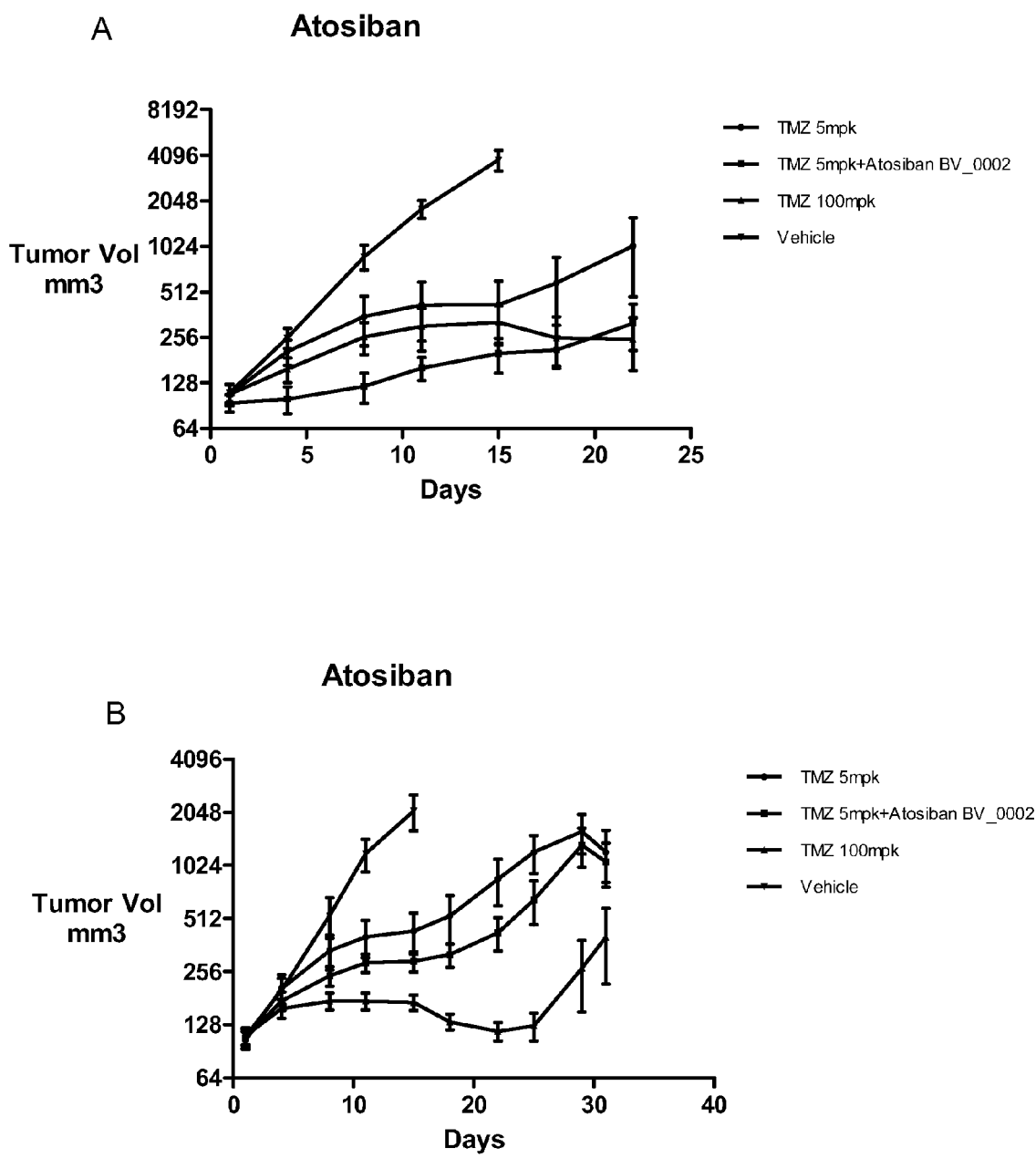
FIGS. 7A and B show tumor growth curves for mice treated with temozolomide and atosiban compared to temozolomide alone and vehicle alone in two separate studies.
Figure 8:
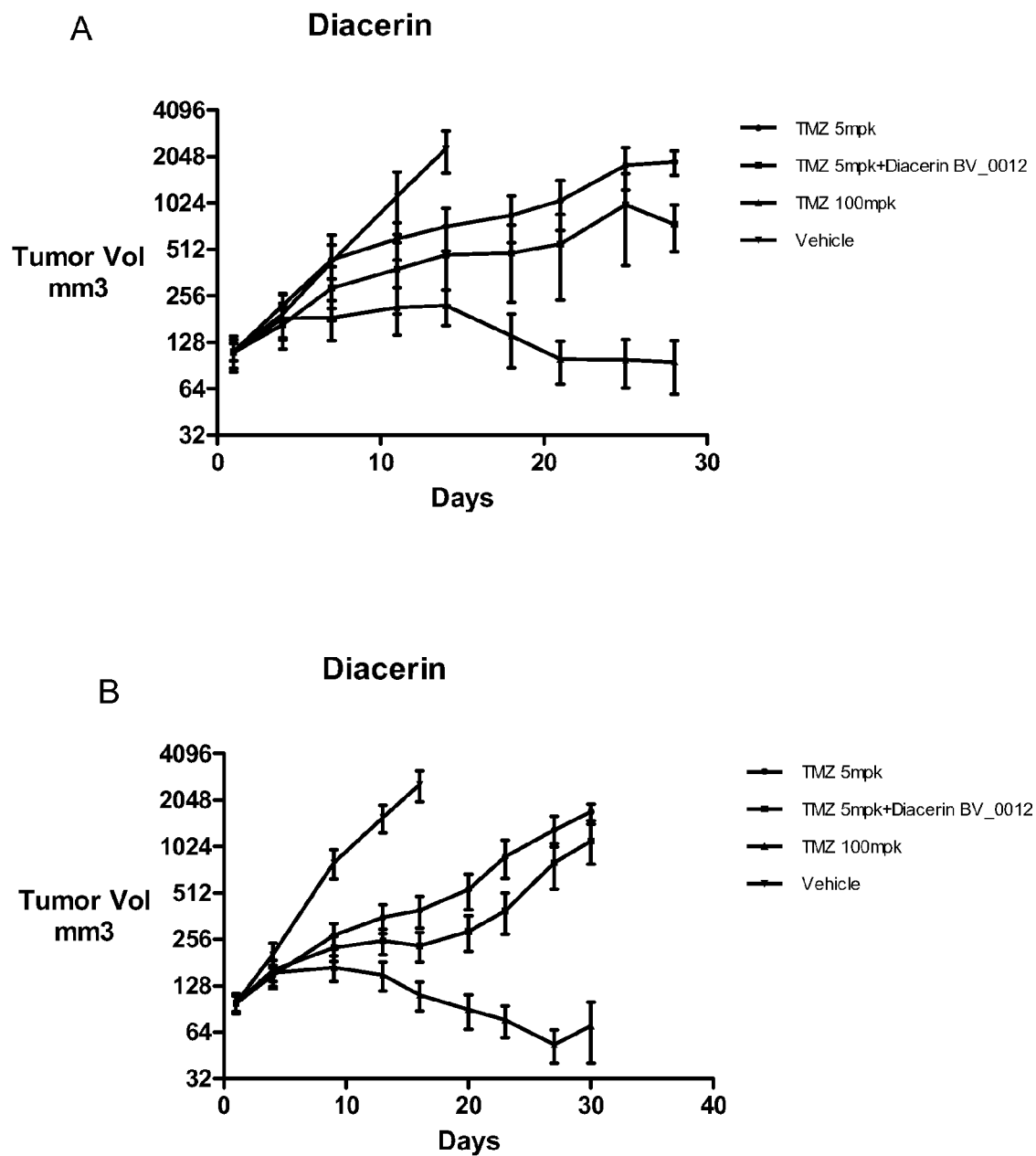
FIGS. 8A and B show tumor growth curves for mice treated with temozolomide and diacerin compared to temozolomide alone and vehicle alone in two separate studies.
Figure 9:
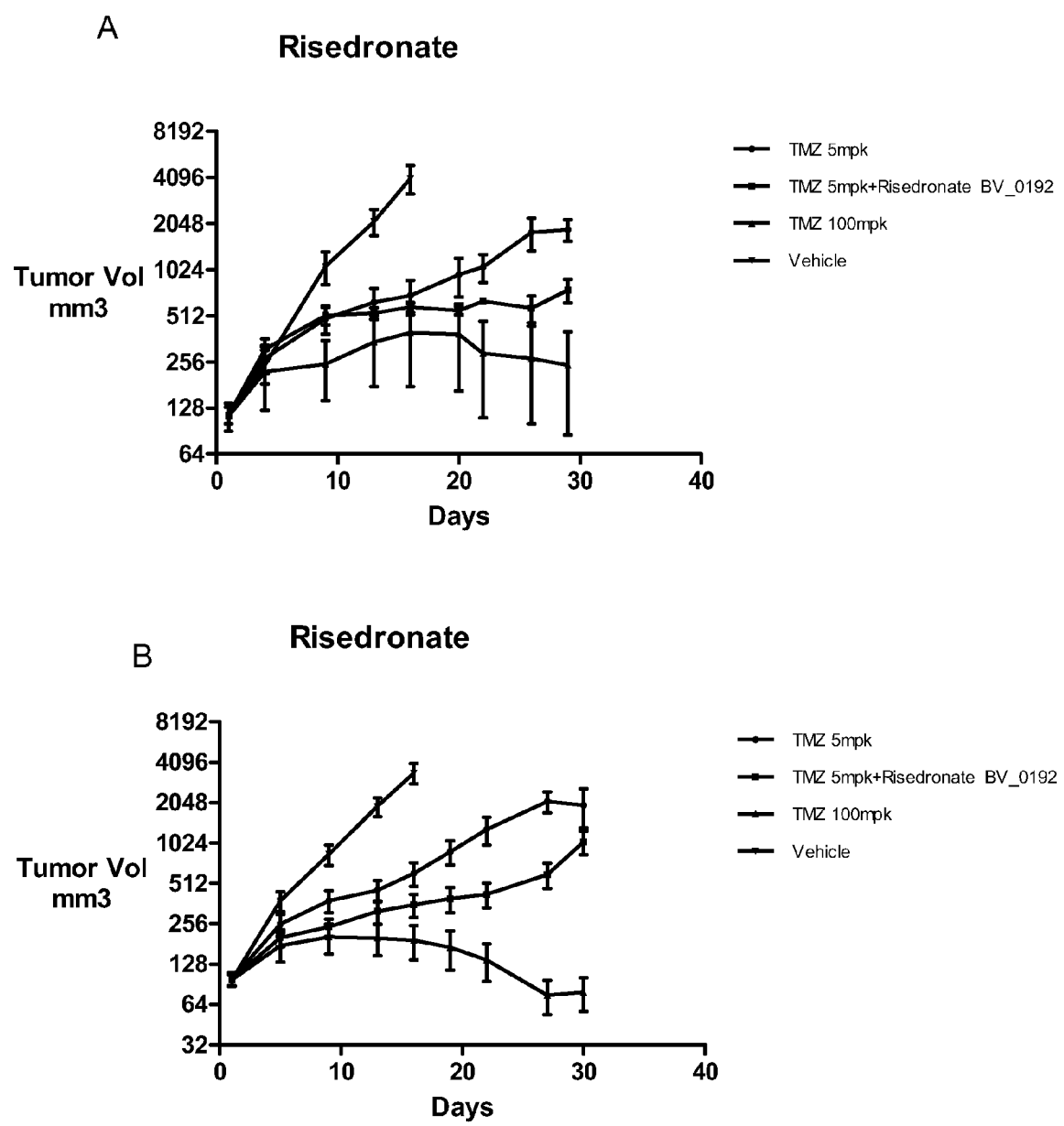
FIGS. 9A and B show tumor growth curves for mice treated with temozolomide and risedronate compared to temozolomide alone and vehicle alone in two separate studies.
Figure 10:
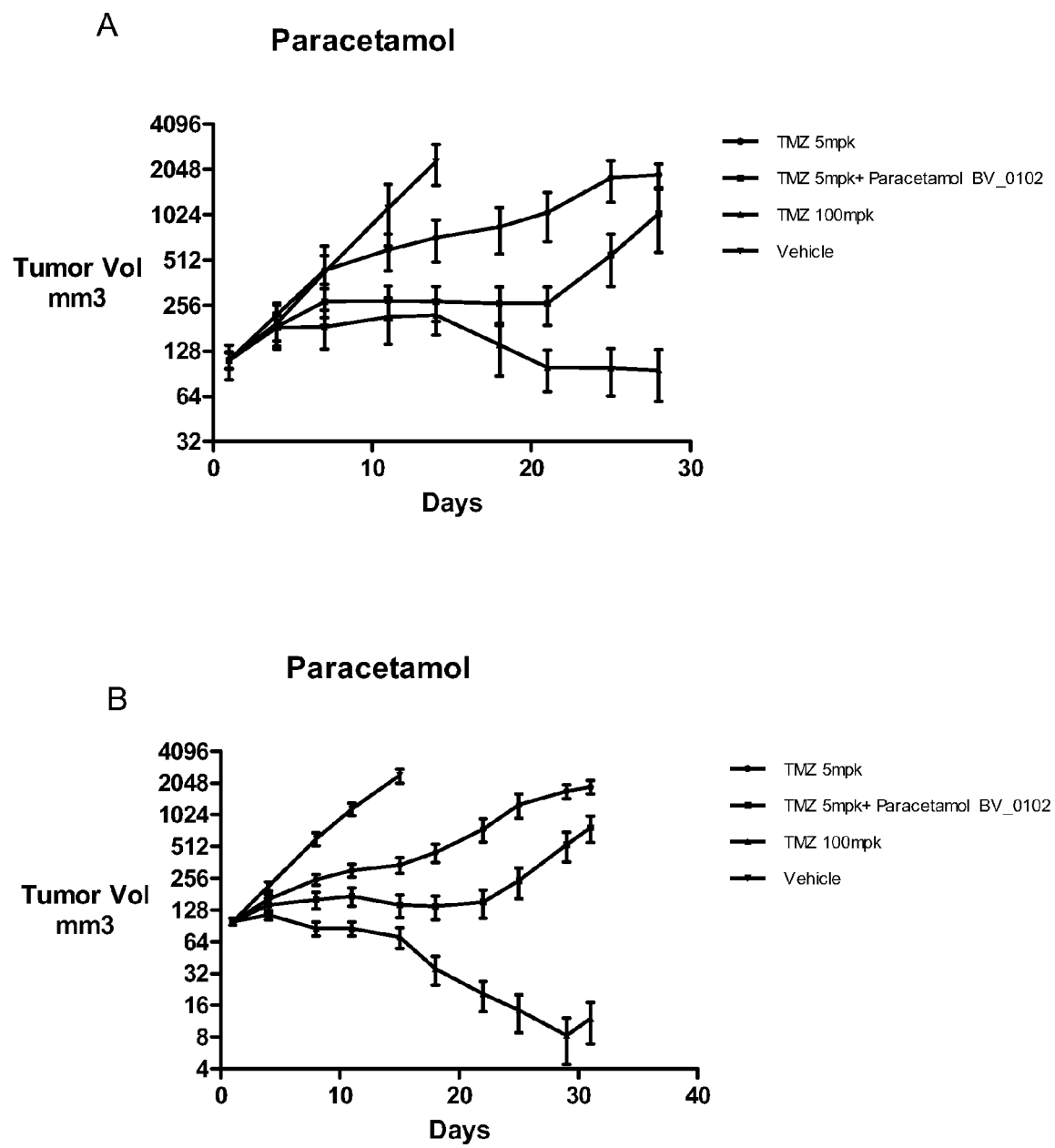
FIGS. 10A and B show tumor growth curves for mice treated with temozolomide and paracetamol compared to temozolomide alone and vehicle alone in two separate studies.
Figure 11:
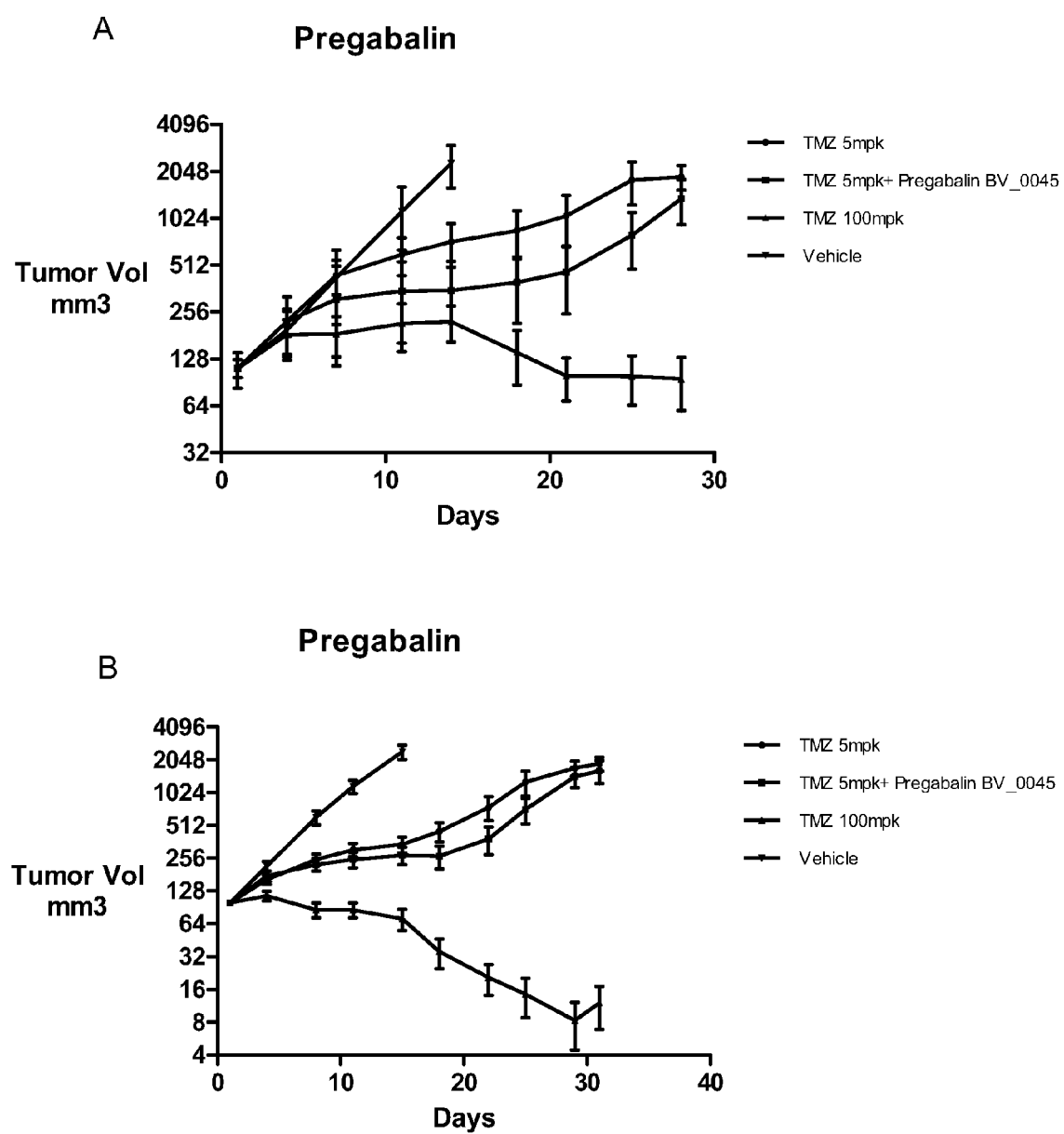
FIGS. 11A and B show tumor growth curves for mice treated with temozolomide and pregabalin compared to temozolomide alone and vehicle alone in two separate studies.
Figure 12:
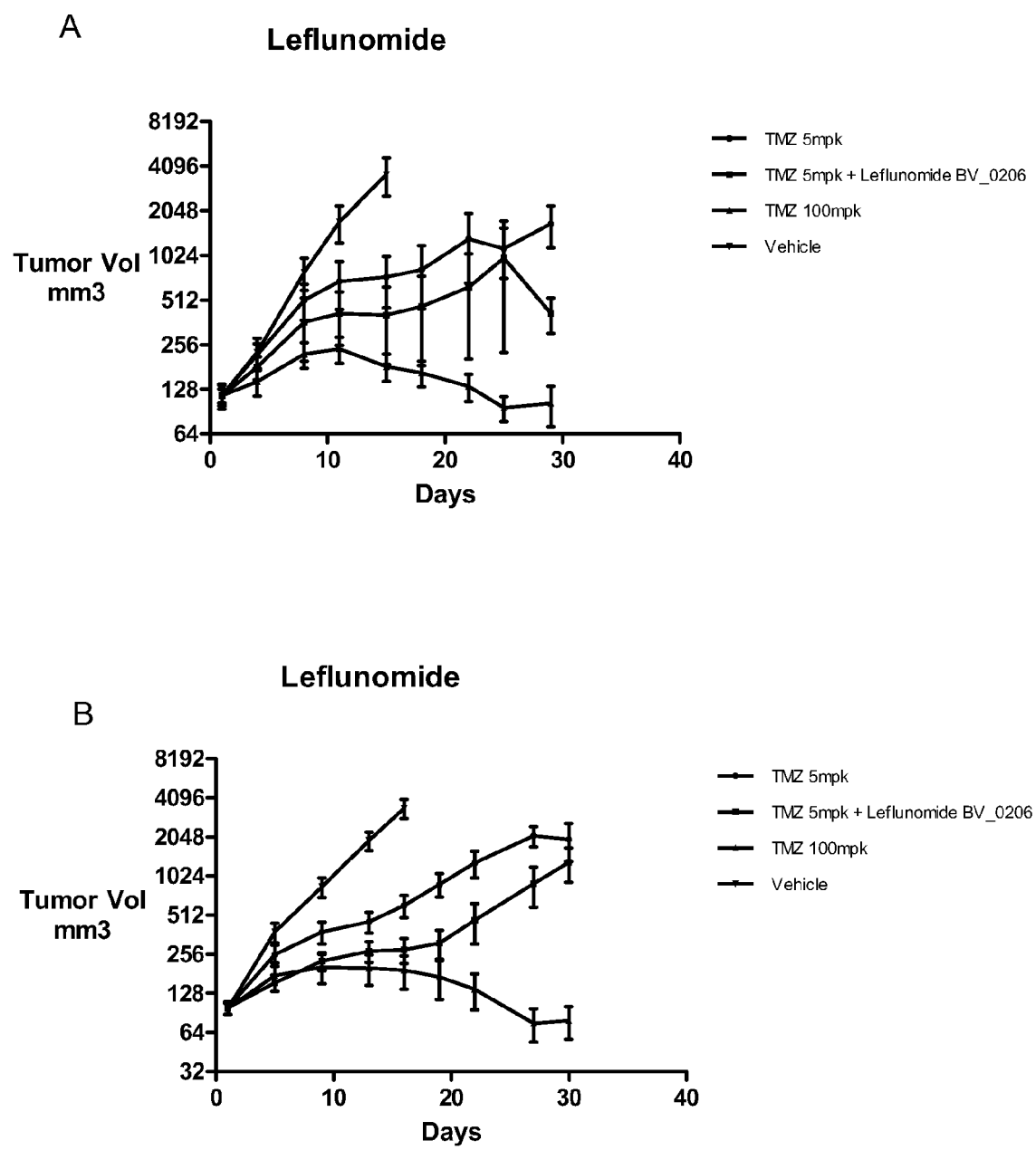
FIGS. 12A and B show tumor growth curves for mice treated with temozolomide and leflunomide compared to temozolomide alone and vehicle alone in two separate studies.
Figure 13:
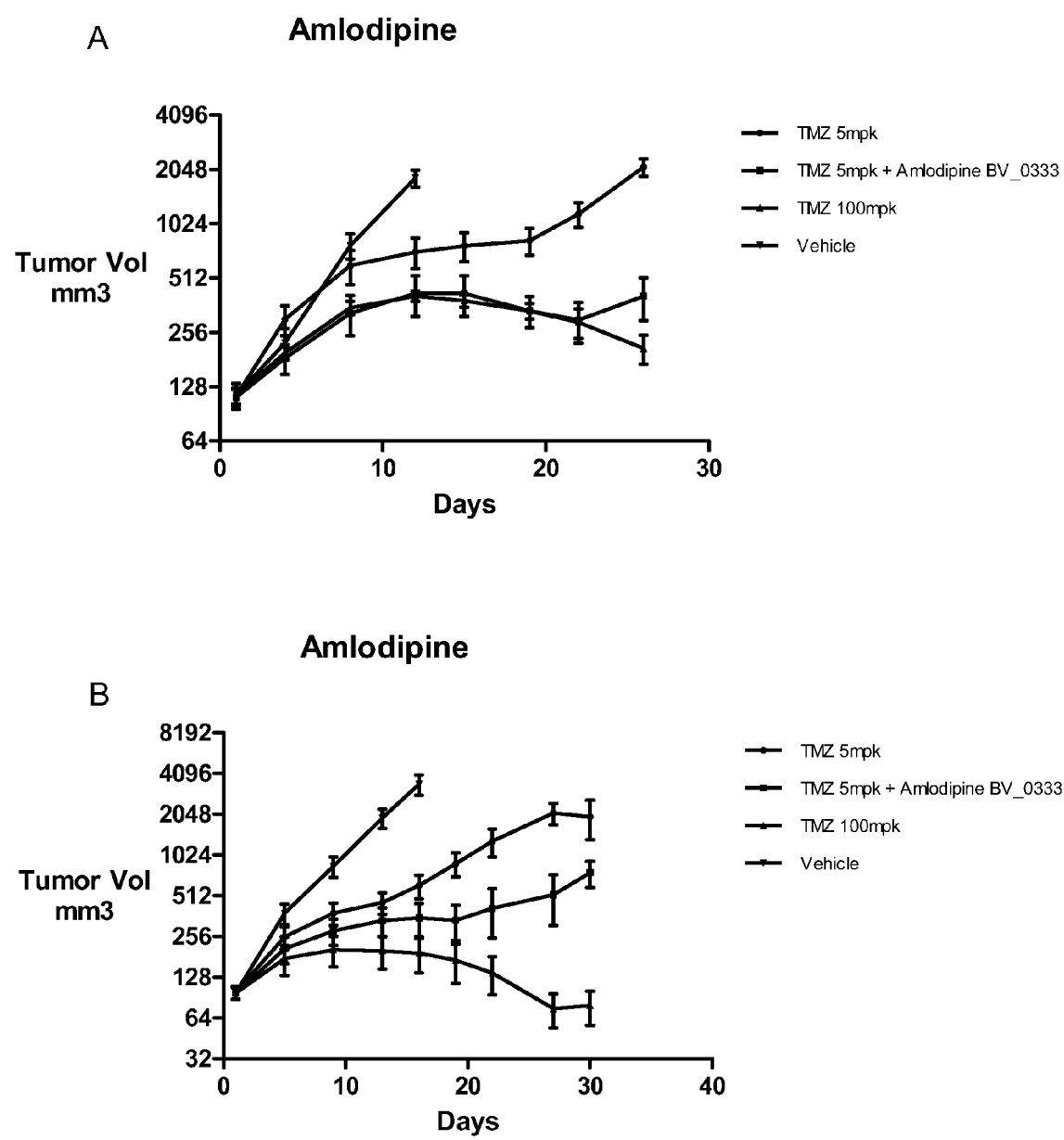
FIGS. 13A and B show tumor growth curves for mice treated with temozolomide and amlodipine compared to temozolomide alone and vehicle alone in two separate studies.
Figure 14:
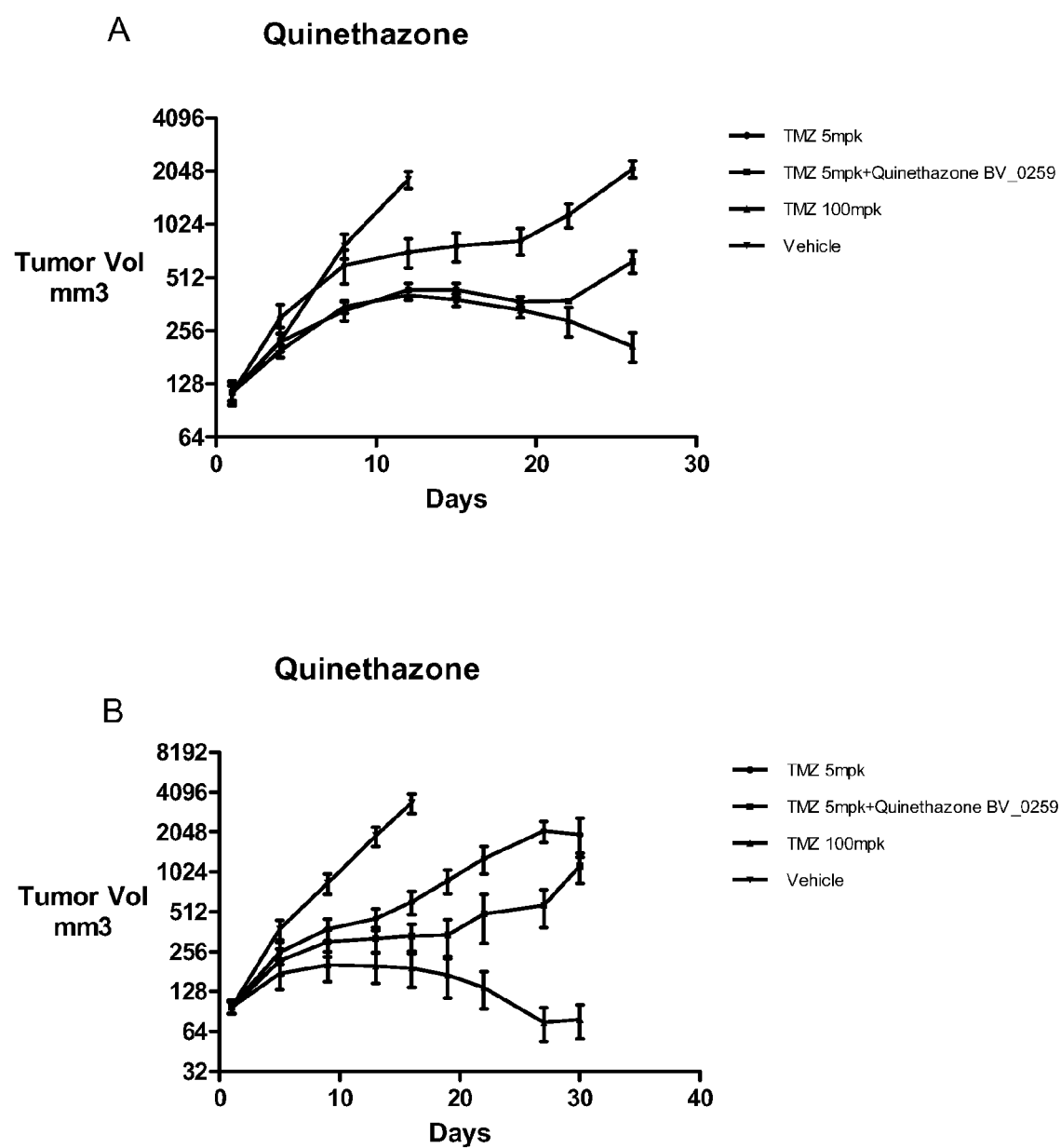
FIGS. 14A and B show tumor growth curves for mice treated with temozolomide and quinethazone compared to temozolomide alone and vehicle alone in two separate studies.
Figure 15:
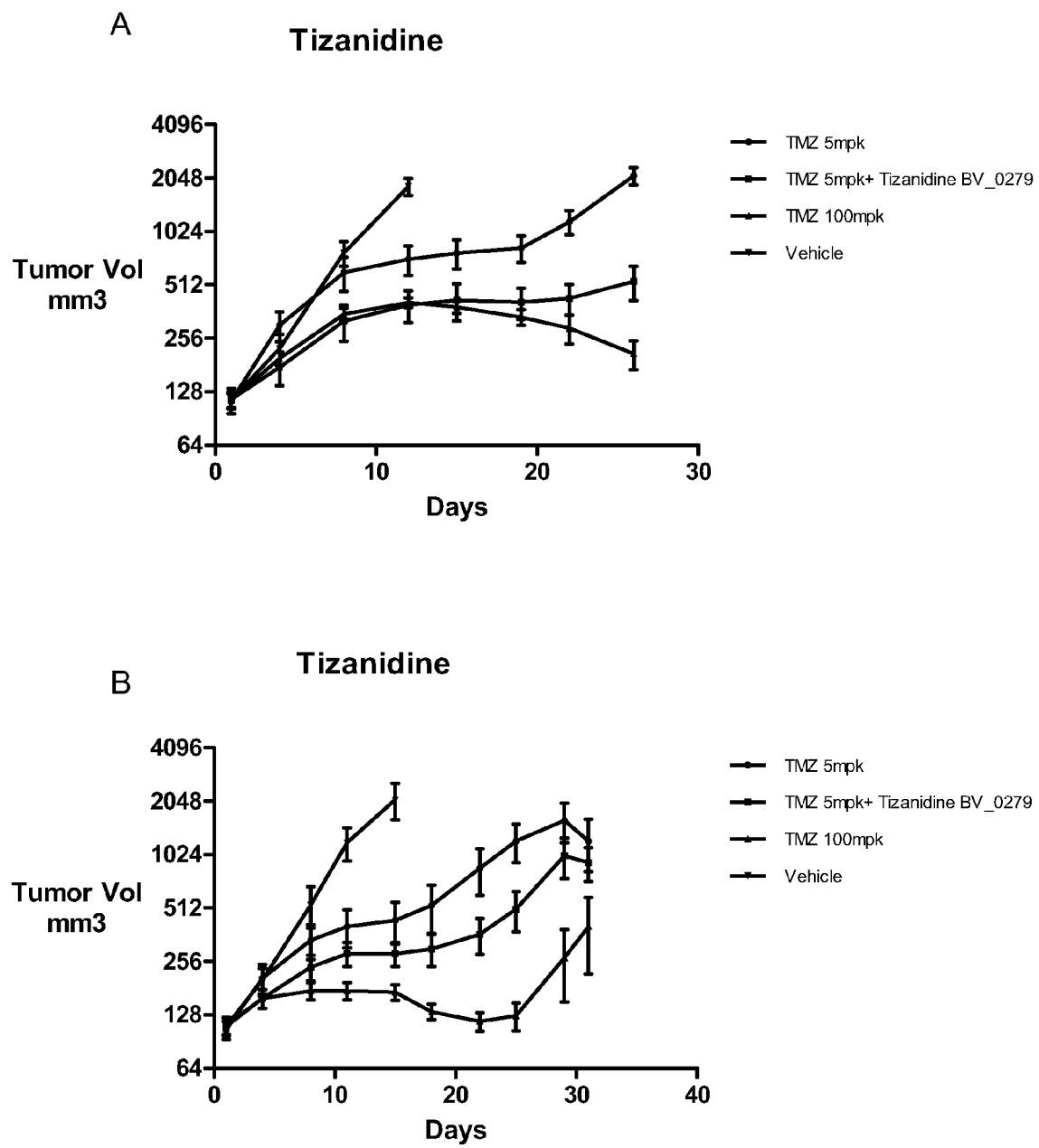
FIGS. 15A and B show tumor growth curves for mice treated with temozolomide and tizanidine compared to temozolomide alone and vehicle alone in two separate studies.
Figure 16:
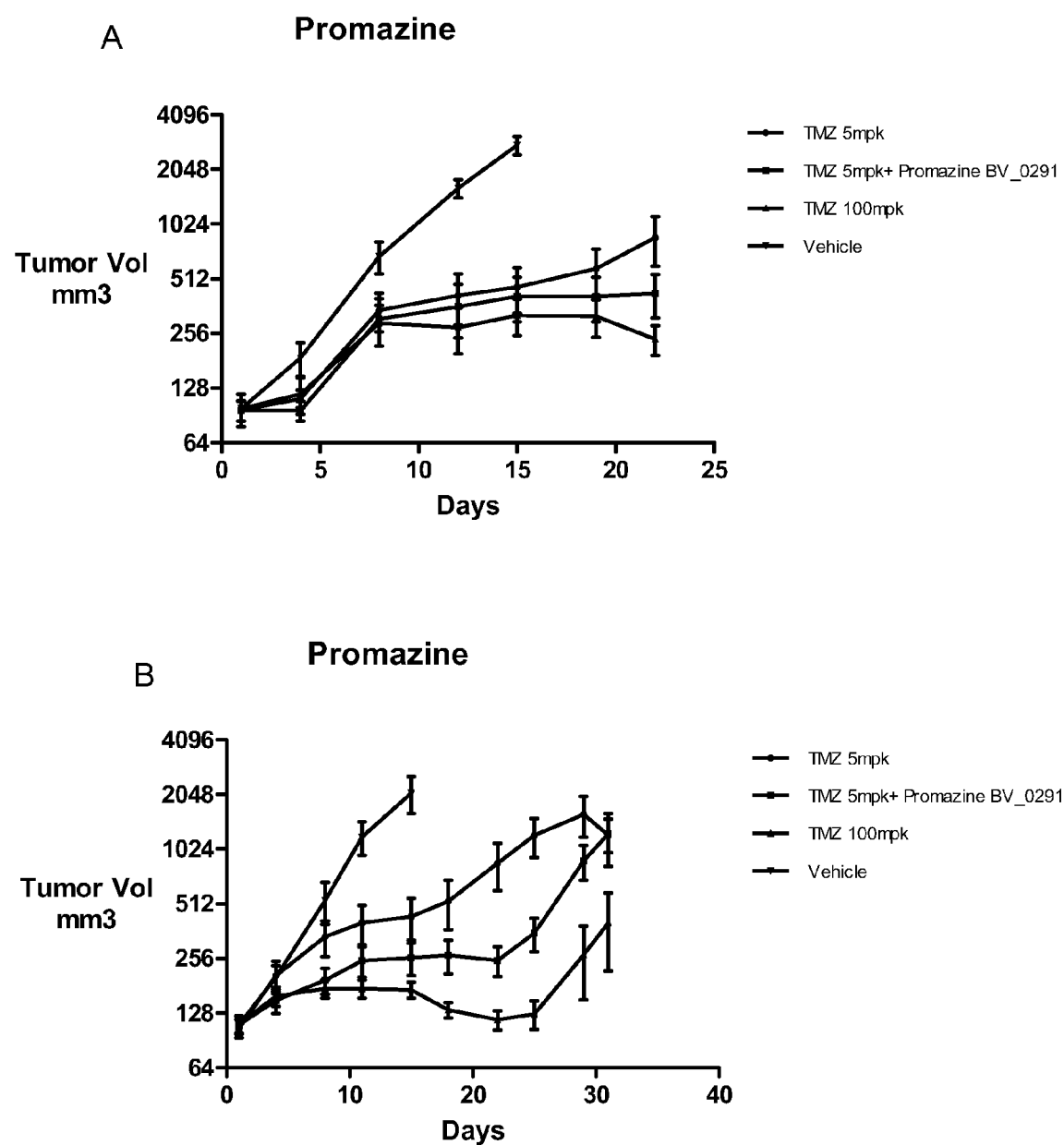
FIGS. 16A and B show tumor growth curves for mice treated with temozolomide and promazine compared to temozolomide alone and vehicle alone in two separate studies.
Figure 17:
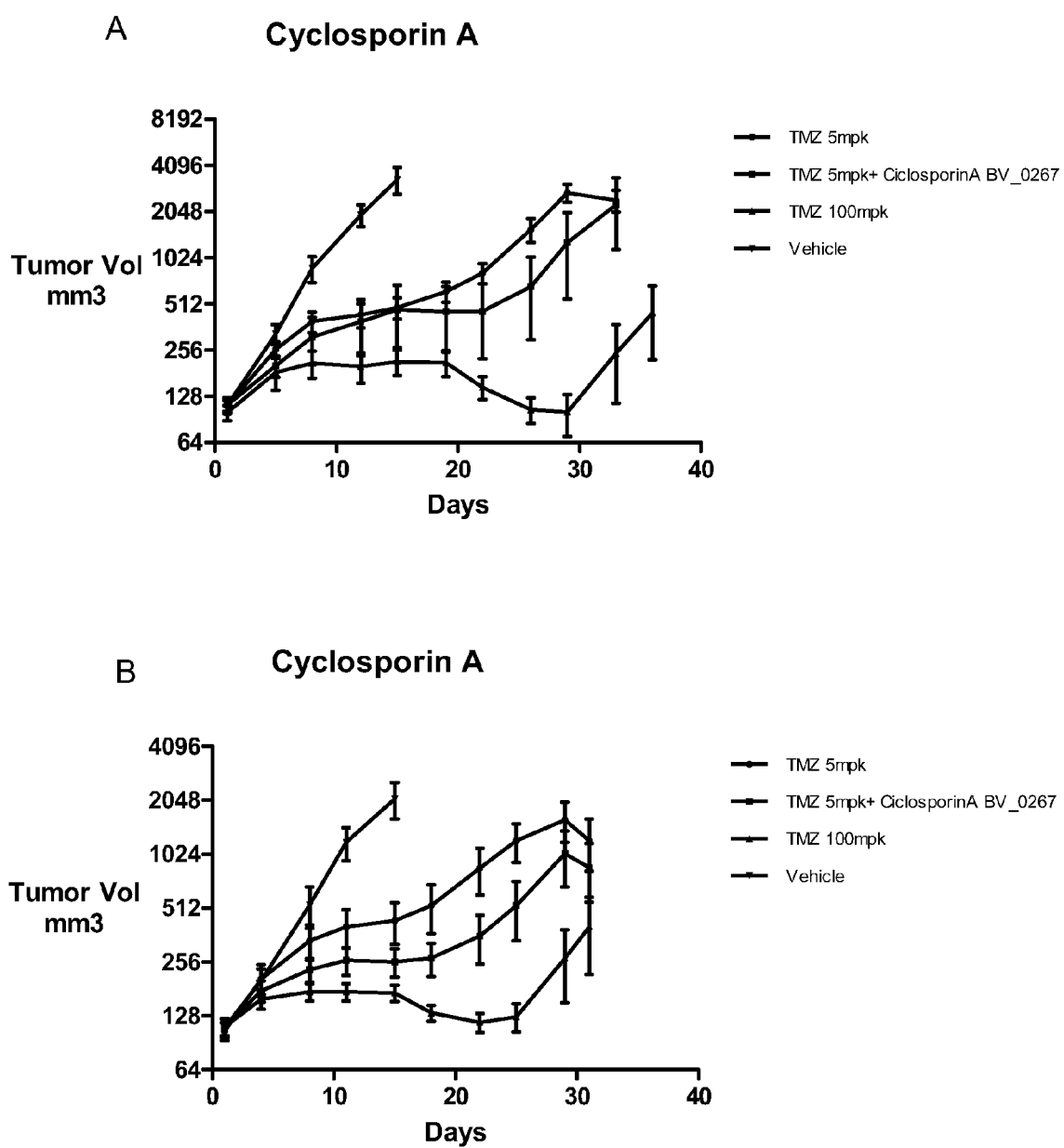
FIGS. 17A and B show tumor growth mice for groups treated with temozolomide and cyclosporin A compared to temozolomide alone and vehicle alone in two separate studies.
Figure 18:
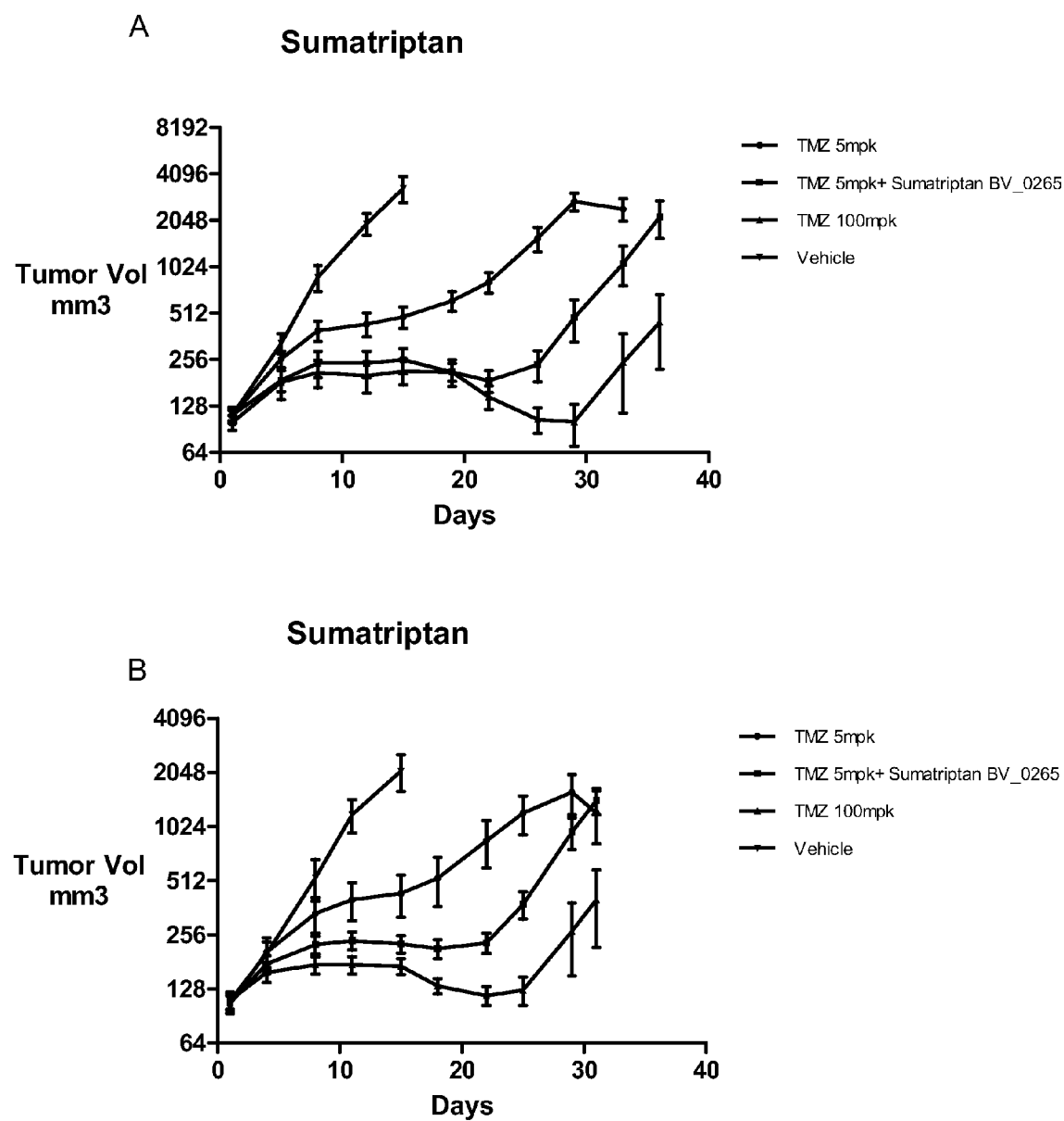
FIGS. 18A and B show tumor growth curves for mice treated with temozolomide and sumatriptan compared to temozolomide alone and vehicle alone in two separate studies.

Study Endpoint = 2000 mm$^3$, Days in Progress = 46
n = number of animals in group
qd x 35 = once daily on Days 1-35
qd x 5 = once daily on Days 1-5
qd x 30 start Day 6 = once daily on Days 6-35
TTE = time to endpoint, T − C = difference between median TTE (days) of treated versus control group, % TGD = [(T − C)/C] × 100
The maximum T − C in this study is 34.6 days (304%), compared with Group 1
Statistical Significance (Logrank test):
ne = not evaluable,
ns = not significant,
* = P < 0.05,
** = P < 0.01,
*** = P < 0.001, compared to group indicated
MTV (n) = median tumor volume (mm3) for the number of animals on the day of TGD analysis (excludes animals attaining tumor volume endpoint)
PR = partial regressions;
CR = total number complete regressions;
TFS = tumor free survivors, i.e., CRs at end of study
Mean BW Nadir = lowest group mean body weight, as % change from Day 1; — indicates no decrease in mean body weight was observed
TR = treatment-related death;
NTR = non-treatment-related death The median TTE of Group 1 untreated controls was 11.4 days, establishing a maximum possible TGD of 34.6 days (304%) for this 46-day study (Table 6). All control tumors progressed to the 2000 mm$^3$ endpoint (Table 6). The scatter plot shows a uniform distribution of calculated TTE values for controls (FIG. 4). The Group 1 mean tumor growth plot illustrates the rapid growth of control tumors (FIGS. 5 and 6).

Group 2 received 5 mg/kg temozolomide p.o. qd×5, and served as the temozolomide monotherapy control for the combinations administered in Groups 3-5. The median TTE of Group 2 was 28.7 days, corresponding to TGD of 17.3 days (152%), with no regressions, but a statistically significant logrank survival advantage compared to control (Group 1 vs. 2, P<0.001). All Group 2 tumors progressed to the 2000 mm$^3$ endpoint volume (Table 6). The Group 2 mean tumor growth plot illustrates the delay compared to control Group 1 (FIGS. 5 and 6).

Group 6 received temozolomide administered at 100 mg/kg p.o. qd×5, and served as the positive control for the experiment. The median TTE of Group 6 was 42.0 days, corresponding to TGD of 30.6 days (268%), with one CR that remained a TFS at study end (Table 6). All Group 6 tumors attained the 2000 mm$^3$ endpoint volume, excluding the TFS (Table 6). Logrank analysis detected a statistically significant survival difference for the 100 mg/kg temozolomide group compared to control (Group 1 vs. 6, P<0.001). The Group 6 mean tumor growth plot indicated noteworthy activity, with a decrease in tumor burden from Days 11 to 27, followed by resumed tumor growth (FIGS. 5 and 6).

Temozolomide (5 mg/kg p.o. qd×5) was administered in combination with candesartan at 10 mg/kg i.p. qd×35 (Group 3), 10 mg/kg i.p. qd×5 (Group 4), or 10 mg/kg i.p. qd×30 start on Day 6 (Group 5), respectively. The median TTEs of Groups 3-5 were 35.4, 31.3 and 30.1 days, respectively, corresponding to TGDs of 24.0 days (211%), 19.9 days (175%) and 18.7 days (164%), respectively (Table 6). All tumors in these three groups progressed to the 2000 mm$^3$ endpoint volume, and no regression responses were recorded (Table 6). However, each combination resulted in a statistically significant logrank survival advantage compared to control (Group 1 vs. 3, 4 or 5, P<0.001). The Group 3 combination showed a statistically significant survival difference compared to the temozolomide monotherapy (Group 2 vs. 3, P<0.001), but survival in combination Groups 4 and 5 did not differ significantly from temozolomide alone (Group 2 vs. 4 or 5, P>0.05). Consistent with the logrank outcomes, TGD in combination Group 3 was 6.7 days longer compared to Group 2, whereas TGD in Groups 4 and 5 differed from Group 2 by 2.6 and 1.4 days, respectively (Table 6). The mean tumor growth plots indicated modestly greater activity for the Group 3 temozolomide/candesartan combination relative to temozolomide alone (FIG. 6, upper panel), and negligible or no difference for the Group 4 and 5 combinations relative to temozolomide alone (FIG. 6, middle and lower panels).

Table 6 also provides a summary of maximum mean BW losses, TR and NTR deaths. All regimens in this study were acceptably tolerated. No TR or NTR deaths were documented, and mean BW losses were negligible or zero in all groups except the positive control group (Group 6), which had an acceptable mean BW nadir of −6.2% on Day 7. No clinical symptoms were recorded in this study.

This experiment evaluated three combinations of candesartan with temozolomide for schedule-related in vivo efficacy in the U87MG human glioblastoma xenograft model.

Control tumors exhibited uniform growth characteristics, progressing to the 2000 mm$^3$ tumor volume endpoint with a median TTE of 11.4 days, yielding a maximum possible TGD of 34.6 days (304%) for this 46-day study. The positive control for this model (100 mg/kg temozolomide p.o. qd×5) resulted in TGD of 30.6 days (268%), with one CR that remained a TFS, and statistically significant logrank survival compared to control (P<0.001). These results were consistent with expected activity.

All test treatments were acceptably tolerated and could be evaluated for efficacy. The 5 mg/kg temozolomide monotherapy resulted in TGD of 17.3 days (152%), with no regressions but significant logrank survival (P<0.001).

The combination of temozolomide (5 mg/kg p.o. qd×5) with candesartan (10 mg/kg i.p. qd×35) produced the greatest TGD among the three combinations evaluated in this study. This was the only combination that offered an advantage over temozolomide alone based upon TGD, logrank survival and mean tumor growth. However, the 24.0-day TGD for this temozolomide/candesartan combination was shorter than the duration of candesartan treatment (35 days). The results for temozolomide (5 mg/kg p.o. qd×5)/candesartan (10 mg/kg i.p. qd×35) in this Example were consistent with those for temozolomide (5 mg/kg p.o. qd×5)/candesartan (10 mg/kg i.p. qd×21) in the previous Example.

When compared to temozolomide alone, the present experiment detected negligible benefit for temozolomide combined with short-term (qd×5) candesartan treatment and no benefit for temozolomide combined with delayed (qd×30 start Day 6) candesartan treatment.

In summary, temozolomide (5 mg/kg p.o. qd×5) combined with candesartan at 10 mg/kg i.p. qd×35 was efficacious, and was the only combination in the experiment that offered an advantage over temozolomide alone.

Methods and Materials

Mice

Female athymic nude mice (nu/nu, Harlan) were 7 to 8 weeks old and had a body weight range of 20.4 to 26.3 grams on Day 1 of the study. The care of the animals are as set forth in the previous Example.

Tumor Implantation

Xenografts were initiated with U87MG human glioblastomas maintained at Piedmont by serial subcutaneous transplantation in athymic nude mice. Each test mouse received a U87MG tumor fragment (1 mm$^3$) implanted subcutaneously in the right flank, and the growth of tumors was monitored as the average size approached the target range of 80 to 120 mm$^3$. Nine days later, designated as Day 1 of the study, the animals were pair matched into six groups each consisting of ten mice with individual tumor volumes ranging from 63 to 144 mm$^3$ and group mean tumor volumes from 101 to 103 mm$^3$. Tumor volume was calculated using the formula:

$$\text{Tumor Volume (mm}^3\text{)} = w^2 \times l$$

where w=width and l=length in mm of a U87MG tumor. Tumor weight may be estimated with the assumption that 1 mg is equivalent to 1 mm$^3$ of tumor volume.

Therapeutic Agents

Candesartan was supplied as a dry powder, which was stored protected from light at room temperature. Candesartan doses were formulated in 0.5% carboxymethyl cellulose (CMC) in deionized water at a concentration of 1 mg/mL to yield the desired 10 mg/kg dosage in a dosing volume of 10 mL/kg, and were stored protected from light at 4° C. for up to one week.

Temozolomide (Temodar®, Schering Corporation, Lot #9RSA003) was prepared by suspending the contents of two 100 mg Temodar® capsules in 20 mL deionized water. This 10 mg/mL stock was used to dose the 100 mg/kg temozolomide group, and was further diluted with deionized water to 0.5 mg/mL for dosing the 5 mg/kg group. The temozolomide dosing solutions were stored at 4° C. protected from light during the 5-day dosing period.

Treatment

On Day 1 of the study, mice were sorted into six groups each consisting of ten mice, and dosing was initiated according to the treatment plan summarized in Table 1. Group 1 mice were not treated and served as controls for calculation of % TGD. Group 2 received 5 mg/kg temozolomide administered orally (p.o.) once daily for five days (qd×5), and served as the monotherapy control for the combination treatments. Groups 3-5 received temozolomide (5 mg/kg p.o. qd×5) in combination with 10 mg/kg candesartan given intraperitoneally (i.p.) on three different schedules: once daily for thirty-five days (qd×35), once daily for five days (qd×5), and once daily for thirty days beginning on Day 6 (qd×30 start Day 6), respectively. Group 6 received 100 mg/kg temozolomide p.o. qd×5, and served as the positive control for the model. All doses were scaled to the body weights of the individual animals.

Endpoint

Tumors were measured twice each week using calipers. Animals were monitored individually, and each mouse was euthanized when its tumor reached the endpoint size of 2000 $mm^3$ or at the conclusion of the study (Day 46), whichever came first. The time to endpoint (TTE) for each mouse was calculated as disclosed in Example 2 above.

Treatment outcome was evaluated by tumor growth delay (TGD), which was also calculated as disclosed in Example 2 above.

Animals were monitored for regression responses. Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 $mm^3$ for one or more of these three measurements. In a CR response, the tumor volume is less than 13.5 $mm^3$ for three consecutive measurements during the course of the study. An animal with a CR response at the termination of a study is additionally classified as a tumor-free survivor (TFS).

Toxicity

Animals were weighed daily on Days 1-5, and then twice weekly until the study was completed. The mice were observed frequently for overt signs of any adverse, treatment-related side effects, and clinical signs of toxicity were recorded when observed. Acceptable toxicity was defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 14 days of the last dose. A death is classified as NTR if there is no evidence that death was related to treatment side effects. NTR deaths may be further characterized based on cause of death. A death may be classified as NTRa if it resulted from an accident or human error. A death may be classified as NTRm if necropsy indicated that it may have resulted from tumor dissemination by invasion and/or metastasis. A death may be classified as NTRu if the cause of death is unknown and there is no available evidence of death related to treatment side effects, metastasis, accident or human error, although death due to treatment side effects cannot be excluded.

Statistical and Graphical Analyses

The logrank test, which evaluates overall survival experience, was used to analyze the significance of the differences between the TTE values of selected groups. The logrank test analyzes the individual TTEs for all animals in a group, except those lost to the study due to NTR death. Two-tailed statistical analyses were conducted at significance level P=0.05. Statistical analyses are not conducted for any group whose treatment is deemed above the MTD. Kaplan-Meier plots were constructed to show the percentage of animals remaining in the study as a function of time. These plots used the same data set as the logrank test.

Mean tumor growth curves show group mean tumor volumes as a function of time, with error bars indicating one standard error of the mean (SEM). When an animal exited the study due to tumor size, the final tumor volume recorded for the animal was included with the data used to calculate the group mean tumor volume at subsequent time points. Mean tumor growth plots were truncated after 50% of the animals in the group had exited the study for tumor volume endpoint.

Prism (GraphPad) for Windows 3.03 was used for all graphic presentations and statistical analyses.

Example 4

Compounds are assessed for combination efficacy in a tumor fragment xenograft model generated by serial passage of a commonly available U87MG glioma human tumor cell line. Experimental cohorts are derived by seeding 8-12 week old, female HRLN nu/nu mice with 1 $mm^3$ sub-fragments of tumors maintained through serial passage in living xenografts. As the xenografted mice reach tumor burdens ranging from 80-120 mg (typically within 5-10 days following seeding), they are randomized to cohorts for chemotherapy treatment. Mice are then dosed with a sub-efficacious dose of temozolomide: dosing is typically at 5 mg/kg, delivered in a 10 mL/kg dose volume via oral gavage in a water vehicle, once-daily for 5 days. To test the effects of combination drug therapy, experimental agents are dosed both concurrently with 5 mg/kg temozolomide, and followed by continued dosing with experimental compounds alone for all days of a study until completion (typically at least 20 days, see the "Schedule" column in table 7 below). Experimental compounds are dosed once daily, in a dose volume less than or equal to 10 mL/kg, in varying vehicle resuspensions and varied routes (see table 7 below). All animals are assessed periodically for body weight, as well as tumor burden using standard protocols with mechanical calipers. Animals with tumor burdens greater than 2000 $mm^3$ are humanely sacrificed; dosing and assessment continues for all mice on protocol until all those animals exposed to experimental compounds reach the tumor burden threshold.

TABLE 7

| Compound | CAS Reg. No., Representative | Route | Dose (mg/kg) | Schedule | Vehicle |
|---|---|---|---|---|---|
| Atosiban | 90779-69-4 | i.v. (intravenous) | 100 | qd × 28 | 0.5% CMC/Saline |
| Diacerein | 13739-02-1 | p.o. | 30 | qd × 28 | 0.5% CMC: 0.8% Tween 80 in DI Water |
| Risedronic acid | 105462-24-6 | i.p. | 15 | qd × 28 | saline |
| Paracetamol | 103-90-2 | i.p. | 300 | qd × 28 | 20% PEG400 in DI water |
| Pregabalin | 148553-50-8 | i.p. | 200 | qd × 28 | Saline |
| Leflunomide | 75706-12-6 | i.p. | 20 | qd × 28 | 0.1% DMSO in saline |
| Amlodipine | 88150-42-9 | i.p. | 10 | qd × 28 | 20% PEG400 in DI water |
| Quinethazone | 73-49-4 | p.o. | 50 | qd × 28 | 0.5% CMC: 0.8% Tween 80 in DI Water |
| Tizanidine | 51322-75-9 | p.o. | 12 | qd × 21 | 0.5% CMC: 0.2% Tween 80 in DI Water |
| Promazine | 58-40-2 | i.p. | 50 | qd × 28 | 5% ethanol in DI water |
| Cyclosporin A | 59865-13-3 | i.p. | 40 | qd × 28 | 5% ethanol: 5% cremophor EL in saline |
| Sumatriptan | 103628-46-2 | i.p. | 50 | qd × 28 | Acidified water |
| Terbinafine | | i.p. | 50 | qd × 21 | 15% HPBCD in DI water |

CMC = carboxymethylcellulose
DI water = deionized water?
DMSO = Dimethyl sulfoxide
HPBCD = Hydroxypropyl B-Cyclodextrin Experimental compounds are scored for efficacy using various data analyses, including manual growth curve inspection, comparison of mean time-to-tumor burden (analogous to C/T analysis), and time-to-event survival analysis by tumor burden. Control arms for comparison include: mice treated once daily with 10 mL/kg dose volume of water vehicle; mice treated once daily for 5 days with 5 mg/kg temozolomide alone; and mice treated once daily for 5 days with temozolomide at 100 mg/kg, which typically elicits a complete response, or elimination of tumor burden, throughout the duration of study.

The results are shown in FIGS. 7-18, as well as tables 8-13 below. Tables 8-13 show that terbinafine in combination with temozolomide is effective in treating gliomas in the mice model. Tables 8-11 below show data from individual mice treated with temozolomide at various doses, temozolomide in combination with terbinafine, and no treatment control. Table 12 shows the summary data from tables 8-11. Table 13 shows a statistical comparison between mice treated with temozolomide (5 mg/kg, po, qd×5) alone and temozolomide (5 mg/kg, po, qd×5) in combination with terbinafine (50 mg/kg, ip, qd×21).

TABLE 8

| Temozolomide (5 mg/kg, po, qd × 5) | | | | | | | | | |
|---|---|---|---|---|---|---|---|---|---|
| | Day of Study | | | | | | | | |
| | 1 TV (mm$^3$) | 4 TV (mm$^3$) | 7 TV (mm$^3$) | 11 TV (mm$^3$) | 14 TV (mm$^3$) | 18 TV (mm$^3$) | 21 TV (mm$^3$) | 25 TV (mm$^3$) | 28 TV (mm$^3$) |
| 1 | 63 | 126 | 196 | 365 | 405 | 405 | 446 | 1008 | 2025 |
| 2 | 63 | 108 | 172 | 172 | 172 | 196 | 288 | 847 | 1437 |
| 3 | 88 | 162 | 352 | 486 | 416 | 567 | 750 | 1764 | 3179 |
| 4 | 88 | 88 | 100 | 162 | 162 | 245 | 245 | 384 | 908 |
| 5 | 88 | 100 | 320 | 288 | 288 | 288 | 365 | 726 | 1470 |
| 6 | 126 | 446 | 847 | 1268 | 1568 | 2025 | 2890 | 2432 | TP on day 25 |
| 7 | 126 | 288 | 500 | 864 | 936 | 1099 | 1183 | 2601 | TP on day 25 |
| 8 | 126 | 172 | 172 | 172 | 288 | 256 | 256 | 550 | 1183 |
| 9 | 126 | 288 | 550 | 550 | 666 | 550 | 600 | 1352 | 3035 |
| 10 | 221 | 446 | 1183 | 1666 | 2304 | 2890 | 3564 | 6292 | TP on day 25 |
| Mean | 111.2 | 222.2 | 439.1 | 599.1 | 720.4 | 852.1 | 1058.6 | 1795.6 | 1890.8 |
| SEM | 14.6 | 43.5 | 109.3 | 162.6 | 222.5 | 287.4 | 375.8 | 554.6 | 339.4 |
| n | 10 | 10 | 10 | 10 | 10 | 10 | 10 | 10 | 7 |

TV = tumor volume
TP = terminal point

TABLE 9

Temozolomide (5 mg/kg, po, qd x 5), terbinafine (50 mg/kg, ip, qd x 21)

| | Day of Study | | | | | | | | |
|---|---|---|---|---|---|---|---|---|---|
| | 1 TV (mm³) | 4 TV (mm³) | 7 TV (mm³) | 11 TV (mm³) | 14 TV (mm³) | 18 TV (mm³) | 21 TV (mm³) | 25 TV (mm³) | 28 TV (mm³) |
| 1 | 63 | 63 | 75 | 75 | 75 | 75 | 75 | 172 | 405 |
| 2 | 108 | 172 | 288 | 405 | 288 | 172 | 108 | 63 | 63 |
| 3 | 108 | 75 | 63 | 108 | 108 | 108 | 108 | 108 | 126 |
| 4 | 108 | 196 | 288 | 320 | 405 | 500 | TR on day 19 | | |
| 5 | 162 | 162 | 320 | 384 | 486 | 352 | NTRu on day 19 | | |
| Mean | 109.7 | 133.4 | 206.7 | 258.4 | 272.4 | 241.3 | 97 | 114 | 197.8 |
| SEM | 15.8 | 27 | 56.7 | 69.8 | 80.5 | 80.5 | 11 | 31.6 | 105.2 |
| n | 5 | 5 | 5 | 5 | 5 | 5 | 3 | 3 | 3 |

TV = tumor volume
TR = treatment related death
NTRu = non-treatment related death

TABLE 10

No Treatment

| | Day of Study | | | | | | | | |
|---|---|---|---|---|---|---|---|---|---|
| | 1 TV (mm³) | 4 TV (mm³) | 7 TV (mm³) | 11 TV (mm³) | 14 TV (mm³) | 18 TV (mm³) | 21 TV (mm³) | 25 TV (mm³) | 28 TV (mm³) |
| 1 | 63 | 108 | 196 | 787 | 1913 | TP on day 14 | | | |
| 2 | 75 | 108 | 126 | 196 | 500 | TP on day 14 | | | |
| 3 | 88 | 144 | 245 | 700 | 2250 | TP on day 14 | | | |
| 4 | 108 | 172 | 288 | 936 | 2025 | TP on day 14 | | | |
| 5 | 221 | 446 | 1268 | 3035 | 4800 | TP on day 14 | | | |
| Mean | 110.7 | 195.4 | 424.5 | 1130.6 | 2297.5 | | | | |
| SEM | 28.5 | 63.7 | 212.5 | 491.9 | 697.1 | | | | |
| n | 5 | 5 | 5 | 5 | 5 | | | | |

TV = tumor volume
TP = terminal point

TABLE 11

Temozolomide (100 mg/kg p.o. qdx5)

| | Day of Study | | | | | | | | |
|---|---|---|---|---|---|---|---|---|---|
| | 1 TV (mm³) | 4 TV (mm³) | 7 TV (mm³) | 11 TV (mm³) | 14 TV (mm³) | 18 TV (mm³) | 21 TV (mm³) | 25 TV (mm³) | 28 TV (mm³) |
| 1 | 63 | 75 | 75 | 108 | 126 | 75 | 63 | 63 | 14 |
| 2 | 75 | 172 | 126 | 126 | 196 | 63 | 63 | 14 | 14 |
| 3 | 88 | 144 | 144 | 100 | 144 | 88 | 75 | 88 | 144 |
| 4 | 108 | 172 | 196 | 256 | 196 | 126 | 75 | 108 | 108 |
| 5 | 221 | 352 | 384 | 486 | 446 | 352 | 221 | 221 | 196 |
| Mean | 110.7 | 182.8 | 185 | 215.2 | 221.5 | 140.6 | 99.1 | 98.4 | 95 |
| SEM | 28.5 | 45.8 | 53.4 | 73.4 | 57.7 | 53.9 | 30.5 | 34.4 | 36.1 |
| n | 5 | 5 | 5 | 5 | 5 | 5 | 5 | 5 | 5 |

TV = tumor volume

TABLE 12

| n | Treatment Regimen | MTV (n) Day 25 | % TGI | Statistical Significance | Regressions PR | Regressions CR | Mean BW Nadir | Deaths TR | Deaths NTR |
|---|---|---|---|---|---|---|---|---|---|
| 10 | Temozolomide (5 mg/kg, po, qd x 5) | 1180 (10) | — | — | 0 | 0 | — | 0 | 0 |
| 4 | Temozolomide (5 mg/kg, po, qd x 5), terbinafine (50 mg/kg, ip, qd x 21) | 108 (4) | 92 | * | 0 | 0 | −0.4% Day 7 | 1 | 1 |

TABLE 12-continued

| n | Treatment Regimen | MTV (n) Day 25 | % TGI | Statistical Significance | Regressions PR | Regressions CR | Mean BW Nadir | Deaths TR | Deaths NTR |
|---|---|---|---|---|---|---|---|---|---|
| 5 | No Treatment | 2025 (5) | −41 | ns | 0 | 0 | — | 0 | 0 |
| 5 | Temozolomide (100 mg/kg, po, qd x 5) | 88 (5) | 94 | ** | 0 | 0 | — | 0 | 0 |

Study Endpoint = 2000 mm³, Days in Progress = 25
n = number of animals in group not dead from accidental or unknown causes, or euthanized for sampling
qd x 5 = once daily on Days 1-5
qd x 21 = once daily on Days 1-21
% TGD = [1 − T/C] x 100 = Percent tumor growth inhibition, compared to the group treated with temozolomide (5 mg/kg, po, qd x 5)
Statistical Significance (Kruskal-Wallis Dunn's test):
ns = not significant,
* = P < 0.05,
** = P < 0.01,
*** = P < 0.001, compared to the group treated with temozolomide (5 mg/kg, po, qd x 5)
MTV (n) = median tumor volume (mm³) for the number of animals on the day of TGI analysis (includes animals with tumor volume at endpoint)
PR = partial regressions;
CR = total number complete regressions;
Mean BW Nadir = lowest group mean body weight, as % change from Day 1; — indicates no decrease in mean body weight was observed
TR = treatment-related death;
NTR = non-treatment-related death

TABLE 13

| Groups compared | Temozolomide (5 mg/kg, po, qd × 5) vs. Temozolomide (5 mg/kg, po, qd × 5), terbinafine (50 mg/kg, ip, qd × 21) |
|---|---|
| Mann-Whitney U test | |
| P value | 0.016 |
| Exact or approximate P value? | Gaussian Approximation |
| P value summary | P ≤ 0.05 |
| Are medians significantly Different? (P < 0.05) | Yes |
| One- or two- tailed P value? | Two-tailed |
| Mann-Whitney U | 30.50 |

Example 5

HRLN female nu/nu mice were seeded with 1 mm³ U87MG tumor fragments subcutaneously in the flank. Final caliper and body weight measurements were taken on the last day of the study.

The age of the mice at the start date of the study was 8 to 12 weeks. As the xenografted mice reach tumor burdens ranging from 80 to 120 mg, they are randomized to cohorts for chemotherapy treatment. The treatment regimen (the agents used, the dose, the route, and the schedule) are shown in Table 14 below. Temozolomide standard of care was dosed for 5 days, either at sub-efficacious (5 mg/kg) or fully efficacious (100 mg/kg) dose levels.

Figure 19:
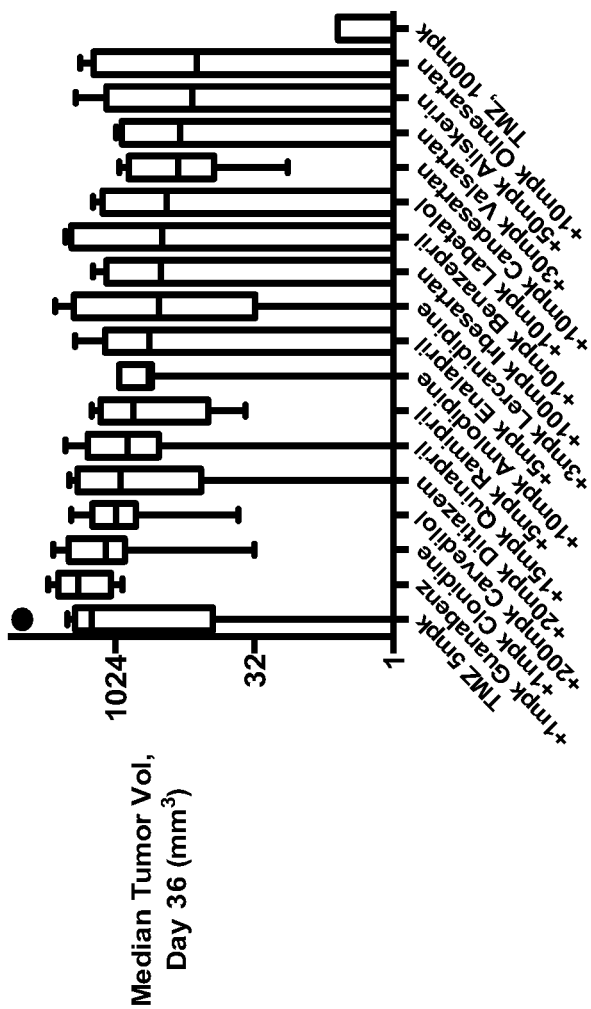
FIG. 19 shows median tumor volume distributions of groups treated with 5 mg/kg temozolomide, a combination of various compounds (as indicated) with 5 mg/kg temozolomide, and 100 mg/kg temozolomide on day 36 of the study.

All animals were assessed periodically for body weight, as well as tumor burden, using standard protocols with mechanical calipers. Any individual animal with a single observation of greater than 30% body weight loss or three consecutive measurements of greater than 25% body weight loss was euthanized. Dosing was stopped for any group with two measurements of mean body weight loss of greater than 20%. The group was not euthanized, and recovery was allowed. Within a group with greater than 20% weight loss, individuals reaching the individual body weight loss endpoint were euthanized. If the group body weight loss was recovered, dosing may resume. If on a designated data collection day, the weight loss for any group exceeded 15%, that group was given a 2 day dosing holiday. Dosing was then resumed with the candidate agent at half the original dose. Animals were monitored as a group. The endpoint of the experiment was a mean tumor weight in control group (or group 1) of 2000 mm³ or 60 days, whichever comes first. When the endpoint was reached, all the animals were euthanized. The results of the study are shown in FIG. 19 and in Table 14.

Plotting median group tumor burden at Day 36 (FIG. 19) shows that several compounds targeting elements of the rennin-angiotensin system provide added efficacy when dosed in combination with temozolomide. Treatments that exhibit tumor growth inhibition (TGI) of greater or equal to 60% indicate therapeutic activity. Generally, it appears that angiotensin receptor blockers (such as candesartan, valsartan, irbesartan, and olmesartan) are as effective as a rennin inhibitor (such as aliskerin). Angiotensin converting enzyme inhibitors (such as ramipril, benazepril, and quinapril) are next in rank-order potency. Calcium channel blockers (such as amlodipine, diltiazem, and lercanidipine) show modest combination effects. Diuretics and alpha-blockers show minimal to no combination effects.

TABLE 14

| Group | Evaluable n | Agent | Dose | Route | Schedule | MTV(n) Day 29 | % TGI | Statistical Significance | Regression PR | Regression CR | Mean BW Nadir | Deaths TR | Deaths NTR |
|---|---|---|---|---|---|---|---|---|---|---|---|---|---|
| 1 | 10 | temozolomide | 5 | po | qd x 5 | 410 (10) | — | — | 0 | 1 | — | 0 | 0 |
| 2 | 8 | temozolomide Candesartan | 5 10 | po ip | qd x 5 qd x 30 | 32 (8) | 92 | ns | 6 | 0 | −0.1% Day 3 | 0 | 0 |

TABLE 14-continued

| Group | Evaluable n | Treatment Regimen | | | | MTV(n) Day 29 | % TGI | Statistical Significance | Regression | | Mean BW Nadir | Deaths | |
|---|---|---|---|---|---|---|---|---|---|---|---|---|---|
| | | Agent | Dose | Route | Schedule | | | | PR | CR | | TR | NTR |
| 3 | 8 | temozolomide<br>Valsartan | 5<br>30 | po<br>ip | qd x 5<br>qd x 30 | 39 (8) | 90 | ns | 0 | 4 | — | 0 | 0 |
| 4 | 8 | temozolomide<br>Carvedilol | 5<br>200 | po<br>po | qd x 5<br>qd x 30 | 126 (8) | 69 | ns | 1 | 0 | — | 0 | 0 |
| 5 | 8 | temozolomide<br>Irbesartan | 5<br>100 | po<br>po | qd x 5<br>qd x 30 | 70 (8) | 83 | ns | 0 | 4 | −0.5%<br>Day 3 | 0 | 0 |
| 6 | 7 | temozolomide<br>Amlodipine | 5<br>10 | po<br>ip | qd x 5<br>qd x 30 | 75 (7) | 82 | ns | 2 | 1 | −1.5%<br>Day 3 | 0 | 1 |
| 7 | 8 | temozolomide<br>Clonidine | 5<br>1 | po<br>ip | qd x 5<br>qd x 30 | 149 (8) | 64 | ns | 3 | 0 | −3.5%<br>Day 3 | 0 | 0 |
| 8 | 8 | temozolomide<br>Olmesartan | 5<br>10 | po<br>po | qd x 5<br>qd x 30 | 27 (8) | 93 | ns | 1 | 3 | −1.9%<br>Day 3 | 0 | 0 |
| 9 | 8 | temozolomide<br>Ramipril | 5<br>5 | po<br>po | qd x 5<br>qd x 30 | 86 (8) | 79 | ns | 4 | 0 | −1.3%<br>Day 3 | 0 | 0 |
| 10 | 8 | temozolomide<br>Enalapril | 5<br>5 | po<br>ip | qd x 5<br>qd x 30 | 54 (8) | 87 | ns | 2 | 3 | — | 0 | 0 |
| 11 | 7 | temozolomide<br>Benazepril | 5<br>10 | po<br>ip | qd x 5<br>qd x 30 | 32 (7) | 92 | ns | 1 | 3 | — | 0 | 1 |
| 12 | 8 | temozolomide<br>Quinapril | 5<br>15 | po<br>po | qd x 5<br>qd x 30 | 86 (8) | 79 | ns | 1 | 1 | −0.4%<br>Day 3 | 0 | 0 |
| 13 | 8 | temozolomide<br>Aliskiren | 5<br>50 | po<br>ip | qd x 5<br>qd x 30 | 48(8) | 88 | ns | 1 | 4 | — | 0 | 0 |
| 14 | 8 | temozolomide<br>Guanabenz | 5<br>1 | po<br>ip | qd x 5<br>qd x 30 | 508 (8) | −24 | ns | 0 | 0 | — | 0 | 0 |
| 15 | 8 | temozolomide<br>Diltiazem | 5<br>20 | po<br>po | qd x 5<br>qd x 30 | 117 (8) | 71 | ns | 0 | 2 | — | 0 | 0 |
| 16 | 8 | temozolomide<br>Lercanidipine | 5<br>3 | po<br>po | qd x 5<br>qd x 30 | 16 (8) | 96 | ns | 2 | 3 | — | 0 | 0 |
| 17 | 8 | temozolomide<br>Labetalol | 5<br>10 | po<br>sc | qd x 5<br>qd x 30 | 76 (8) | 81 | ns | 3 | 3 | — | 0 | 0 |
| 19 | 8 | temozolomide | 100 | po | qd x 5 | 10 (8) | 98 | *** | 1 | 7 | −2.5%<br>Day 8 | 0 | 0 |

Study Endpoint = 2000 mm$^3$; Study Duration = 57 Days
n = number of animals in a group not dead from accidental or unknown causes, or euthanized for sampling
% TGI = [1 − (MTV$_{drug}$ treated/MTV$_{control}$)] × 100 = percent tumor growth inhibition, compared to Group 1
Statistical Significance (Mann-Whitney U test):
ne = not evaluable,
ns = not significant,
* = P ≤ 0.05,
** = P ≥ 0.0 1,
*** = P ≤ 0.001, compared to Group 1
MTV (n) = median tumor volume (mm$^3$) for the number of animals on the day of TGI analysis (includes animals with tumor volume at endpoint)
PR = partial regression;
CR = complete regression
Mean BW Nadir = lowest group mean body weight, as % change from Day 1; — indicates no decrease in mean body weight was observed
TR = treatment-related death;
NTR = non-treatment-related death All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating or ameliorating the effects of a glioma comprising administering to a subject in need thereof an effective amount of candesartan or pharmaceutically acceptable salt thereof, and an effective amount of temozolomide or pharmaceutically acceptable salt thereof.

2. The method according to claim 1 wherein the candesartan is candesartan cilexetil.

3. The method according to claim 2, wherein the candesartan cilexetil is administered at about 2-32 mg per day.

4. The method according to claim 1, wherein the temozolomide is administered at about 50-200 mg/m$^2$ per day.

5. The method according to claim 1, wherein the glioma is an astrocytoma.

6. The method according to claim 5, wherein the astrocytoma is a glioblastoma.

7. The method according to claim 1, wherein the candesartan and temozolomide are administered as part of a pharmaceutical composition.

8. A method for treating or ameliorating the effects of a glioblastoma comprising co-administering to a subject in need thereof an effective amount of a first active agent selected from the group consisting of candesartan and a pharmaceutically acceptable salt thereof, and a second active agent, which is temozolomide or a pharmaceutically acceptable salt thereof.

* * * * *